United States Patent
Alshafei et al.

(10) Patent No.: US 10,550,048 B2
(45) Date of Patent: Feb. 4, 2020

(54) MULTIPLE-STAGE CATALYST SYSTEM FOR SELF-METATHESIS WITH CONTROLLED ISOMERIZATION AND CRACKING

(71) Applicant: Saudi Arabian Oil Company, Dhahran (SA)

(72) Inventors: Faisal H. Alshafei, Khobar (SA); Munir D. Khokhar, Khobar (DE); Noor A. Sulais, Dhahran (SA); Mohammed R. Alalouni, Dammam (SA); Sohel K. Shaikh, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 15/873,421

(22) Filed: Jan. 17, 2018

(65) Prior Publication Data

US 2018/0208524 A1    Jul. 26, 2018

Related U.S. Application Data

(60) Provisional application No. 62/448,478, filed on Jan. 20, 2017.

(51) Int. Cl.
*B01J 29/48* (2006.01)
*C07C 2/12* (2006.01)
(Continued)

(52) U.S. Cl.
CPC .................. *C07C 2/12* (2013.01); *C07C 2/10* (2013.01); *C07C 11/06* (2013.01); *C07C 11/08* (2013.01); *B01J 29/48* (2013.01)

(58) Field of Classification Search
CPC . B01J 29/40; B01J 29/48; B01J 29/005; B01J 29/0308; B01J 29/0341;
(Continued)

(56) References Cited

U.S. PATENT DOCUMENTS 3,442,821 A * 5/1969 Hilfman ............... B01J 2/08
 502/8
3,546,313 A  12/1970 Banks
(Continued)

FOREIGN PATENT DOCUMENTS

CN     102325742 A   1/2012
CN     101531558 B   4/2013
(Continued)

OTHER PUBLICATIONS

Hu et al (NPL: Highly active doped mesoporous KIT-6 catalyst for metathesis of 1-butene and ethane to propene: the influence of neighboring environment of W species, American Chemical Society,117, pp. 26385-26395 (Year: 2013).*
(Continued)

*Primary Examiner* — Melvin C. Mayes
*Assistant Examiner* — Smita S Patel
(74) *Attorney, Agent, or Firm* — Dinsmore & Shohl LLP

(57) ABSTRACT

Embodiments of processes and multiple-stage catalyst systems for producing propylene comprising introducing a hydrocarbon stream comprising 2-butene to an isomerization catalyst zone to isomerize the 2-butene to 1-butene, passing the 2-butene and 1-butene to a metathesis catalyst zone to cross-metathesize the 2-butene and 1-butene into a metathesis product stream comprising propylene and $C_4$-$C_6$ olefins, and cracking the metathesis product stream in a catalyst cracking zone to produce propylene. The isomerization catalyst zone comprises a silica-alumina catalyst with a ratio by weight of alumina to silica from 1:99 to 20:80. The metathesis catalyst comprises a mesoporous silica catalyst support impregnated with metal oxide. The catalyst cracking zone comprises a mordenite framework inverted (MFI) structured silica catalyst.

11 Claims, 3 Drawing Sheets

(51) Int. Cl.
  *C07C 2/10* (2006.01)
  *C07C 11/08* (2006.01)
  *C07C 11/06* (2006.01)

(58) Field of Classification Search
  CPC .... B01J 29/035; B01J 29/0358; B01J 35/006;
    B01J 35/108; B01J 35/1042; B01J
    35/1047; B01J 35/109; B01J 35/1061;
    B01J 35/1057; B01J 35/1019; B01J
    35/1023; B01J 35/023; B01J 37/0201;
    B01J 2229/20; C07C 2529/40; C07C
    2529/48; C07C 2529/03; C07C 2529/035;
    C07C 11/08; C07C 11/06; C07C 11/10;
    C07C 2/12; C07C 2/10; C07C 4/06
  See application file for complete search history.

(56) References Cited

U.S. PATENT DOCUMENTS

| | | |
|---|---|---|
| 3,586,731 A | 6/1971 | Heckelsberg |
| 3,702,886 A | 11/1972 | Argauer et al. |
| 4,024,201 A | 5/1977 | Takahashi |
| 4,071,471 A | 1/1978 | Banks et al. |
| 4,575,575 A | 3/1986 | Drake et al. |
| 4,609,769 A | 9/1986 | Kukes et al. |
| 5,026,935 A | 6/1991 | Leyshon et al. |
| 5,026,936 A | 6/1991 | Leyshon et al. |
| 5,191,131 A | 3/1993 | Takahata et al. |
| 6,207,115 B1 | 3/2001 | Chodorge et al. |
| 6,538,168 B1 | 3/2003 | Schwab et al. |
| 6,586,649 B1 | 7/2003 | Botha et al. |
| 6,646,172 B1 | 11/2003 | Schwab et al. |
| 6,777,582 B2 | 8/2004 | Gartside et al. |
| 6,977,321 B1 | 12/2005 | Dath et al. |
| 7,214,841 B2 | 5/2007 | Gartside et al. |
| 7,754,647 B2 | 7/2010 | Schubert et al. |
| 7,754,934 B2 | 7/2010 | Tsunoda et al. |
| 7,977,522 B2 | 7/2011 | Takai et al. |
| 8,299,313 B2 | 10/2012 | Takai et al. |
| 8,324,440 B2 | 12/2012 | Popp et al. |
| 8,440,874 B2 | 5/2013 | Ramachandran et al. |
| 8,586,813 B2 | 11/2013 | Ramachandran et al. |
| 8,722,568 B2 | 5/2014 | Popp et al. |
| 9,834,497 B2 | 12/2017 | Shaikh et al. |
| 9,884,794 B2 | 2/2018 | Al-Khattaf et al. |
| 2003/0176754 A1 | 9/2003 | Gartside et al. |
| 2004/0254411 A1 | 12/2004 | Steinbrenner et al. |
| 2005/0014981 A1 | 1/2005 | Gartside et al. |
| 2006/0293548 A1 | 12/2006 | Spamer et al. |
| 2007/0038010 A1 | 2/2007 | Xie et al. |
| 2007/0225478 A1 | 9/2007 | Querci et al. |
| 2008/0171655 A1 | 7/2008 | Creyghton et al. |
| 2010/0041930 A1 | 2/2010 | Gartside et al. |
| 2010/0168487 A1* | 7/2010 | Sawyer ............... C07C 6/04 585/324 |
| 2010/0234542 A1 | 9/2010 | Blackborow et al. |
| 2011/0021858 A1 | 1/2011 | Ramachandran et al. |
| 2011/0152595 A1 | 6/2011 | Takai et al. |
| 2011/0196185 A1 | 8/2011 | Krawczyk et al. |
| 2012/0108864 A1* | 5/2012 | Gartside ............... C07C 4/06 585/250 |
| 2012/0264990 A1 | 10/2012 | Nicholas et al. |
| 2012/0283090 A1 | 11/2012 | Popp et al. |
| 2012/0289617 A1 | 11/2012 | Wang et al. |
| 2013/0085311 A1 | 4/2013 | Youn et al. |
| 2013/0165701 A1 | 6/2013 | Zhou et al. |
| 2014/0148629 A1 | 5/2014 | van Hal et al. |
| 2015/0141721 A1* | 5/2015 | Choi ............... B01J 8/0453 585/315 |
| 2016/0237006 A1 | 8/2016 | Stoyanova et al. |
| 2017/0001925 A1 | 1/2017 | Abudawoud et al. |
| 2017/0001926 A1 | 1/2017 | Shaikh et al. |
| 2017/0001927 A1 | 1/2017 | Al-Khattaf et al. |
| 2018/0057425 A1 | 3/2018 | Shaikh et al. |

FOREIGN PATENT DOCUMENTS

| | | |
|---|---|---|
| CN | 104370676 A | 2/2015 |
| DE | 10013253 A1 | 9/2001 |
| EP | 304515 B1 | 12/1991 |
| EP | 0920911 A1 | 6/1999 |
| EP | 2151424 A1 | 2/2010 |
| JP | 2003500190 A | 1/2003 |
| JP | 2012500304 A | 1/2012 |
| WO | 9929805 A1 | 6/1999 |
| WO | 00/71255 A1 | 11/2000 |
| WO | 2006089957 A1 | 8/2006 |
| WO | 2009117128 A1 | 9/2009 |
| WO | 2010019595 A2 | 2/2010 |
| WO | 2008136280 A1 | 7/2010 |
| WO | 2011136983 A1 | 11/2011 |
| WO | 2015055594 A1 | 4/2015 |
| WO | 2017-003812 A1 | 1/2017 |
| WO | 2017/003817 A1 | 1/2017 |
| WO | 2017/003821 A1 | 1/2017 |

OTHER PUBLICATIONS

Kumar et al (NPL: Performance of nano crystalline H-ZSM-5 as additive in FCC catalyst: A review, May 2014, IJRET, vol. 3 pp. 481-485 (Year: 2014).*
Korean Office Action pertaining to Korea Application No. 10-2018-7003238 dated May 14, 2018 (English Translation).
U.S. Office Action dated Apr. 20, 2018 pertaining to U.S. Appl. No. 15/859,794, filed Jan. 2, 2018.
International Search Report and Written Opinion dated Apr. 24, 2018 pertaining to International Application No. PCT/US2018/014131, filed Jan. 18, 2018.
Notice of Allowance dated Apr. 24, 2018 pertaining to U.S. Appl. No. 15/190,964, filed Jun. 23, 2016.
Election/Restriction Requirement dated May 21, 2018, pertaining to U.S. Appl. No. 15/866,772, filed Jan. 10, 2018.
International Search Report and Written opinion dated Mar. 28, 2018, pertaining to International Application No. PCT/US2018/013945, filed Jan. 17, 2018, 9 pages.
Arudra et al., "Silicalite-1 as Efficient Catalyst for Production of Propene from 1-Butene", ACS Catalysis, 2014, 4205-4212, 4, American Chemical Society.
Awayssa et al., "Modified HZSM-5 as FCC Additive for Enhancing Light Olefins Yield from Catalytic Cracking of VGO", Applied Catalysis A: General, 2014, 172-183, 477.
Balcar, et al., Mesoporous molecular sieves as advanced supports for olefin metathesis catalysts, Coordination Chemistry Reviews 257, 2013, pp. 3107-3124, Czech Republic.
Barrett et al., "The Determination of Pore Volume and Area Distributions in Porous Substances. I. Computations from Nitrogen Isotherms", J. Am. Chem. Soc., 1951, 373-380, 73(1).
Beck et al., "A New Family of Mesoporous Molecular Sieves Prepared with Liquid Crystal Templates", J. Am. Chem. Soc., 1992, 10834-10843, 114, American Chemical Society.
Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.
Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.
Bin Hu, et al., Highly Active Doped Mesoporous KIT-6 Catalysts for Metathesis of 1-Butene and Ethene to Propene: The Influence of Neighboring Environment of W Species, The Journal of Physical Chemistry, ACS Publication, 2013 American Chemical Society, pp. 26385-26395, USA.
Daniell et al., Enhanced Surface Acidity in Mixed Alumina-Silicas: A Low-Temperature FTIR Study:, 2000, 196, 247-260, Elsevier.
Do et al., "Zeolite Nanoclusters Coated onto the Mesopore Walls of SBA-15", J. Am. Chem. Soc., 2004, 14324-14325, 126, American Chemical Society.

(56) References Cited

OTHER PUBLICATIONS

International Search Report and Written Opinion dated Nov. 11, 2016 pertaining to International Application No. PCT/US2016/039025.
International Search Report and Written Opinion dated Sep. 14, 2016 pertaining to International Application No. PCT/US2016/039012.
International Search Report and Written Opinion dated Sep. 27, 2016 pertaining to International Application No. PCT/US2016/0038967.
International Search Report and Written Opinion dated Sep. 14, 2016 pertaining to International Application No. PCT/US2016/039013.
Jermy et al., "Utilization of ZSM-5/MCM-41 Composite as FCC Catalyst Additive for Enhancing Propylene Yield from VGO Cracking", J. Porous Mater, 2012, 499-509, 19, Springer.
Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.
Kumar et al., Performance of Nano Crystalline H-ZSM-5 as Additive in FCC Catalyst: A Review, International Journal of Research in Engineering and Tehnology, May 2014, vol. 3, pp. 481-485.
Lwin et al., "Olefin Metathesis by Supported Metal Oxide Catalysts", ACS Catalysis, 2014, 2505-2520, 4, American Chemical Society.
Office Action pertaining to U.S. Appl. No. 15/190,950 dated Sep. 27, 2017.
Office Action pertaining to U.S. Appl. No. 15/190,964 dated Nov. 2, 2017.
Quignard et al., "Aryloxide Ligands in Metathesis of Olefins and Olefinic Esters: Catalytic Behaviour ofW(OAr)2Cl4 by SnMe4, Sn(n-Bu)4, Pb(n-Bu)4, MgNp2: synthesis of W(OAr)2Cl2(CHCMe3)(OR2) and W(OAr)2Cl(CHCMe3)(CH2CMe3)(OR2)", Journal of Molecular Catalysis, 1986, 36, 13-29.
Ruihua Gao, et al., High-activity, single-site mesoporous WO3-MCF materials for the catalytic epoxidation of cycloocta-1,5-diene with aqueous hydrogen peroxide, Journal of Catalysis, 256, 2008, pp. 259-267, China.
Wang et al., Synthesis and Structure of Silicalite-1/SBA-15 Composites Prepared by Carbon Templating and Crystallization, Journal of Materials Chemistry, 2007,4265-4273,17, The Royal Society of Chemistry 2007.
Wang et al., "Effect of Support Nature on WO3/SiO2 Structure and Butene-1 Metathesis", Applied Catalysis A: General, 2003, 25-37, 250, Elsevier B.V.
Zhao et al., "Effect of Tungsten Oxide Loading on Metathesis Activity of Ethene and 2-Butene Over WO3/SiO2 Catalysts" Transition Met Chem, 2009, 621-27, 34, Springer.
International Preliminary Report on Patentability dated Jan. 2, 2018 pertaining to International PCT Application No. PCT/US2016/039012.
International Preliminary Report on Patentability dated Jan. 11, 2018 pertaining to International PCT Application No. PCT/US2016/038967.
Non-Final Office Action pertaing to U.S. Appl. No. 15/398,196 dated Jan. 9, 2018.
Puriwat, et al., "Elucidation of the basicity dependence of 1-butene isomerization on MgO/Mg(OH)s catalysts", Catalysis Communications, 2010, pp. 80-85.
Office Action pertaining to U.S. Appl. No. 15/866,800 dated Jun. 29, 2018.
U.S. Non-Final Office Action dated Jan. 9, 2018 pertaining to U.S. Appl. No. 15/398,196.
Examination Report pertaining to GCC Application No. 2016/31672 dated Sep. 13, 2018.
Office Action dated Jan. 31, 2019 pertaining to U.S. Appl. No. 15/866,800 filed Jan. 10, 2018 (34 pg).
Notice of Allowance dated Mar. 5, 2019 pertaining to U.S. Appl. No. 15/866,772, filed Jan. 10, 2018.
European Search Report for Application No. 19163840.2 dated Aug. 2, 2019.
Chinese Office Action for Application No. 201811179717.1 dated Jun. 13, 2019.
Office Action dated Jun. 18, 2019 pertaining to Korean Patent Application No. 10-2018-7003251.
Office Action dated Mar. 30, 2019 pertaining to Japanese Patent Application No. 2017-567370.
Office Action dated Apr. 4, 2017 pertaining to U.S. Appl. No. 15/190,981, filed Jun. 23, 2016, 14 pgs.
Office Action dated Aug. 28, 2018 pertaining to U.S. Appl. No. 15/866,772, filed Jan. 10, 2018, 41 pgs.
Harmse et al., "On the Product Formation in 1-Butene Mehathesis over Supported Tungsten Catalysts", Catal. Lett., 137; p. 123-131, 2010.
Shaikh, et al., "Self-Methathesis of Butenes to Propylene", Catalysis in Petroleum Refining & Petrochemicals, pp. 1-6, Dec. 7-8, 2015.
Debecker, et al., "Preparation of MoO3/SiO2—Al2O3 methathesis catalysts via wet impregnation with different Mo precursors", Journal of Molecular Catalysis A: Chemical, 340, pp. 65-76, 2011.
Wu, et al., "Investigation on acidity of zeolites bound with silica and alumina", Studies in Surface Science and Catalysis, 143, pp. 217-225, 2002.
Notice of Allowance and Fee(s) Due dated May 15, 2019 pertaining to U.S. Appl. No. 16/156,616, filed Oct. 10, 2018, 35 pgs.
U.S. Office Action dated Jun. 14, 2019 pertaining to U.S. Appl. No. 15/866,800, filed Jan. 10, 2018, 38 pgs.
Office Action dated Apr. 29, 2019 pertaining to U.S. Appl. No. 16/039,983, filed Jul. 19, 2018, 36 pgs.
Yuan Guimei et al., Machine translation of CN 104370676, dated Feb. 2015.
Office Action dated May 2, 2019 pertaining to U.S. Appl. No. 15/859,794, filed Jan. 2, 2018, 30 pgs.
Office Action dated May 2, 2019 pertaining to U.S. Appl. No. 16/156,634, filed Oct. 10, 2018, 32 pgs.
Notice of Allowance and Fee(s) Due dated Aug. 29, 2019 pertaining to U.S. Appl. No. 15/859,794, filed Jan. 2, 2018, 22 pgs.
Examination Report for Application No. GC 2018/34631 dated Aug. 22, 2019.
Decision of Rejection pertaining to Japanese Application No. 2017-567370 dated Sep. 4, 2019.

* cited by examiner

MULTIPLE-STAGE CATALYST SYSTEM FOR SELF-METATHESIS WITH CONTROLLED ISOMERIZATION AND CRACKING

CROSS-REFERENCE TO RELATED APPLICATIONS

This application claims the benefit of U.S. Provisional Application Ser. No. 62/448,478 filed Jan. 20, 2017, incorporated herein by reference.

TECHNICAL FIELD

Embodiments of the present disclosure generally relate to propylene production, and more specifically relate to converting butene to propylene using a multiple-stage catalyst system comprising isomerization, metathesis, and cracking catalysts.

BACKGROUND

In recent years, there has been a dramatic increase in the demand for propylene to feed the growing markets for polypropylene, propylene oxide and acrylic acid. Currently, most of the propylene produced worldwide (74 million tons/year) is a by-product from steam cracking units (57%) which primarily produce ethylene, or a by-product from Fluid Catalytic Cracking (FCC) units (30%) which primarily produce gasoline. These processes cannot respond adequately to a rapid increase in propylene demand.

Other propylene production processes contribute about 12% of total propylene production. Among these processes are propane dehydrogenation (PDH), metathesis reactions requiring both ethylene and butene, high severity FCC, olefins cracking and methanol to olefins (MTO). However, propylene demand has exceeded ethylene and gasoline/distillate demand, and propylene supply has not kept pace with this increase in propylene demand.

SUMMARY

Accordingly, ongoing needs exist for improved processes for the selective production of propylene using multiple-stage catalyst systems. Embodiments of the present disclosure are directed to propylene production from butenes by a multiple-stage catalyst system.

In one embodiment, a process for the production of propylene is provided. The process comprises introducing a hydrocarbon stream comprising 2-butene to an isomerization catalyst zone to isomerize the 2-butene to 1-butene, where the isomerization catalyst zone comprises a silica-alumina catalyst with a ratio by weight of alumina to silica from 1:99 to 20:80. The process also includes passing the 2-butene and 1-butene to a metathesis catalyst zone to cross-metathesize the 2-butene and 1-butene into a metathesis product stream comprising propylene, unconverted $C_4$, and higher metathesis product $C_5$ and $C_6$ olefins, where the metathesis catalyst comprises a mesoporous silica catalyst support impregnated with metal oxide. The process further includes cracking the metathesis product stream in a catalyst cracking zone to produce propylene, where the catalyst cracking zone comprises a mordenite framework inverted (MFI) structured silica catalyst.

In another embodiment, a multiple-stage catalyst system for producing propylene from from a hydrocarbon stream comprising 2-butene is provided. The multiple-stage catalyst system comprises an isomerization catalyst zone, a metathesis catalyst zone downstream of the isomerization zone, and a cracking catalyst zone downstream of the metathesis catalyst zone. The isomerization catalyst zone comprises a silica-alumina catalyst with a ratio by weight of alumina to silica from 1:99 to 20:80, where the silica-alumina catalyst zone isomerizes the 2-butene to 1-butene. The metathesis catalyst zone comprises a mesoporous silica catalyst support impregnated with metal oxide to form a mesoporous silica catalyst, where the mesoporous silica catalyst zone cross-metathesizes the 2-butene and 1-butene into a metathesis product stream comprising propylene, unconverted $C_4$, and higher metathesis product $C_5$ and $C_6$. The cracking catalyst zone comprises a mordenite framework inverted (MFI) structured silica catalyst, where the cracking catalyst zone cracks the metathesis product stream to produce propylene.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Figure 1:
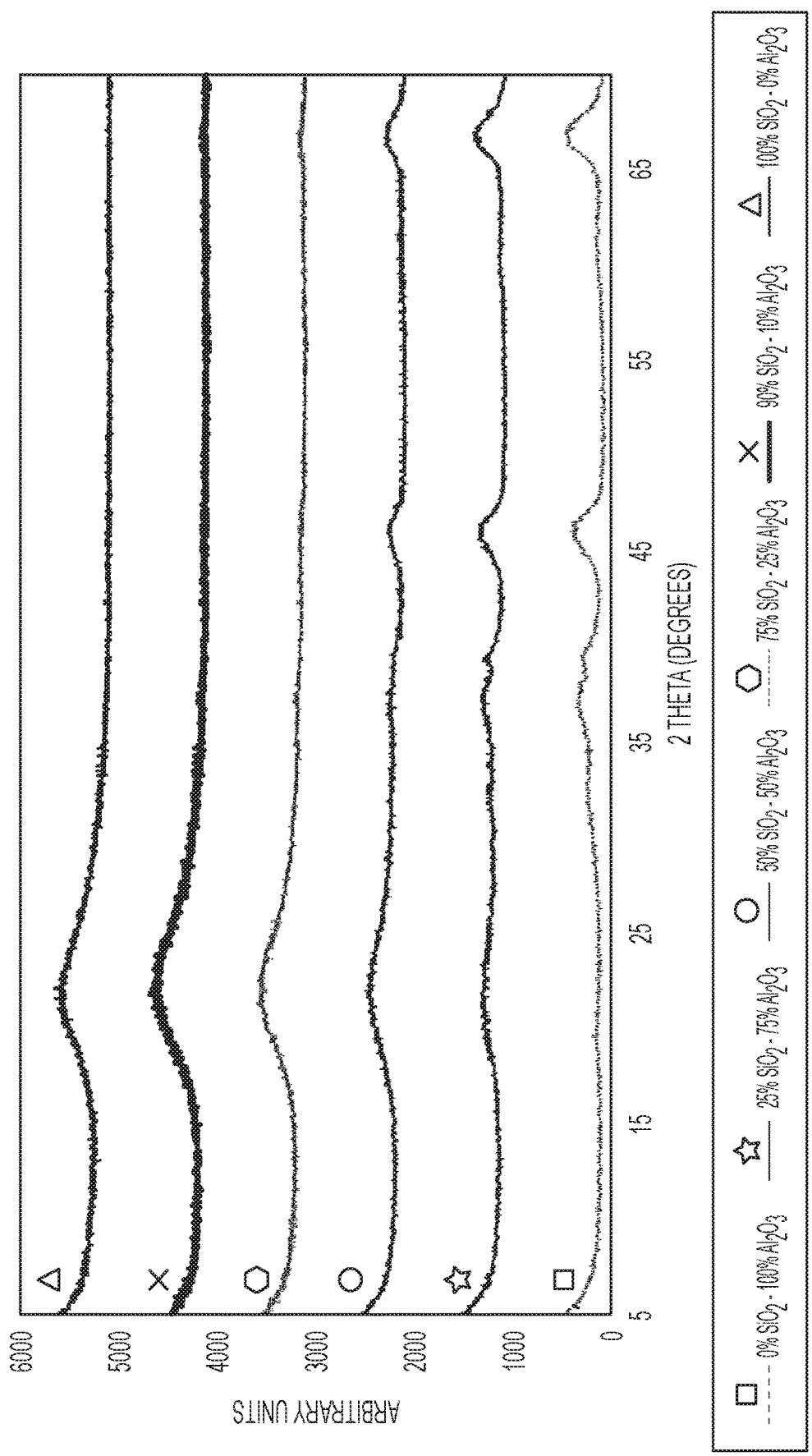
FIG. 1 is an X-ray Powder Diffraction (XRD) graph illustrating the XRD profile of silica-alumina catalysts with varying silica to alumina ratios, in accordance with one or more embodiments of the present disclosure.

Embodiments of the present disclosure are directed to systems and methods for converting a hydrocarbon stream comprising 2-butene to a stream comprising propylene by catalyzed butene isomerization, catalyzed metathesis, and catalyzed cracking. Specifically, the present embodiments are related to a multiple-stage (for example, three-stage) catalyst system containing isomerization, metathesis, and cracking catalysts for greater propylene ($C_3$=) production from a butene stream. While a three-stage catalyst system with 3 catalysts is used throughout this disclosure for simplicity and clarity, it may be appreciated that the multiple-stage catalyst system may include more than 3 catalysts including 4 catalysts, 5 catalysts, or 6 or more catalysts. In one or more embodiments, the isomerization catalyst is followed by the metathesis catalyst, and the metathesis catalyst is followed by the cracking catalyst to provide a greater yield of propylene, and optionally a greater combined yield of propylene and ethylene.

The hydrocarbon stream may be any stream comprising 2-butene. For example, the hydrocarbon stream may be a raffinate stream created from a naphtha cracking process or an FCC stream. Such a stream may be a Raffinate 1 stream, a Raffinate 2 stream or a Raffinate 3 stream. Raffinate 1 is the residual stream which is obtained when a $C_4$ stream from a naphtha cracking process or from a gas cracking process, for example, is subjected to the removal of 1,3-butadiene therefrom. The $C_4$ stream typically contains, as its chief components, n-butene, 1-butene, 2-butene, isobutene and 1,3-butadiene, and optionally some isobutane with the chief components together forming up to 99% or more of the $C_4$ stream. Removal typically may be by extractive distillation with an aprotic solvent such as acetonitrile, N-methylpyrrolidone or N,N-dimethylformamide. Any remaining butadiene after extractive distillation may optionally being removed by an additional treatment such as selective hydrogenation. The resulting and remaining residual stream stream is a Raffinate 1 stream and contains 1-butene, 2-butene and isobutene. A Raffinate 2 stream in turn is a mixture of 1-butene and 2-butene which remains when a Raffinate 1 stream has the isobutene separated therefrom. The separation may be by hydrogenation to tert-butanol in the presence of sulphuric acid, by reaction of the Raffinate 1 stream with methanol to synthesize methyl tert-butyl ether, or by oligomerization or polymerization of the isobutene, for example. Further, a Raffinate 3 stream is what is obtained when the 1-butene in a Raffinate 2 stream is separated therefrom. The seperation may be by fractionation, extractive distillation or molecular sieve absorption, for example. The residual stream of cis 2-butene and trans 2-butene is the Raffinate 3 stream.

In one or more embodiments, the hydrocarbon stream is a Raffinate 2 stream from a fluid catalytic cracker or an ethylene cracker. The Raffinate 2 stream may comprise various compositions. Non-limiting examples of Raffinate 2 stream compositions include 45 to 55 weight percentage (wt %) 1-butene, 20 to 30 wt % 2-butene, 10 to 20 wt % n-butane, 5 to 15 wt % iso-butane, and 0 to 5 wt % other components; 10 to 20 wt % 1-butene, 20 to 30 wt % 2-butene, 8 to 18 wt % n-butane, 37 to 47 wt % iso-butane, and 0 to 8 wt % other components; 48 to 50 weight percentage (wt %) 1-butene, 25 to 37 wt % 2-butene, 14 to 16 wt % n-butane, 9 to 10 wt % iso-butane, and 0 to 1 wt % other components; 15 to 17 wt % 1-butene, 25 to 27 wt % 2-butene, 11 to 13 wt % n-butane, 41 to 44 wt % iso-butane, and 2 to 6 wt % other components; approximately 49.6 wt % 1-butene, approximately 26.0 wt % 2-butene, approximately 14.7 wt % n-butane, approximately 9.4 wt % iso-butane, and approximately 0.3 wt % other components; or approximately 15.6 wt % 1-butene, approximately 26.2 wt % 2-butene, approximately 12.0 wt % n-butane, approximately 42.1 wt % iso-butane, and approximately 4.1 wt % other components As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, and fluidized bed reactors. One or more "reaction zones" may be disposed in a reactor. As used in this disclosure, a "reaction zone" refers to an area where a particular reaction takes place in a reactor. For example, a packed bed reactor with multiple catalyst beds may have multiple reaction zones, where each reaction zone is defined by the area of each catalyst bed.

As shown in Formula 1 as follows, isomerization of 2-butenes to 1-butenes forms an equilibrium as denoted by the bi-directional arrow. The isomerization is achieved with the isomerization catalyst. Then cross-metathesis is achieved as shown in Formula 2 with the metathesis catalyst. Cross-metathesis is an organic reaction that entails the redistribution of fragments of alkenes by the scission and regeneration of carbon-carbon double bonds. In the case of 2-butene and 1-butene, the redistribution results in propylene and $C_5$-$C_6$ olefins. Propylene may also be formed from a secondary cross-metathesis reaction between ethylene and 2-butene as shown in Formula 1. The metathesis catalyst can also result in "self-metathesis" as shown in Formula 4. Without wishing to be bound by theory, it is believed 1-butene reacts with itself due to moderate or less active sites providing room to react with itself instead of forming an isomer such as 2-butene. However, the tendency of cross-metathesis occurring is much higher that self-metathesis. Further, as shown in Formula 5, "catalyzed cracking" refers to the conversion of mainly $C_5/C_6$ alkenes and unconverted $C_4$'s from the metathesis reaction to propylene and ethylene ($C_2$= and $C_3$=), some light gases ($C_1$, $C_2$), and also some higher hydrocarbons depending on cracking conditions.

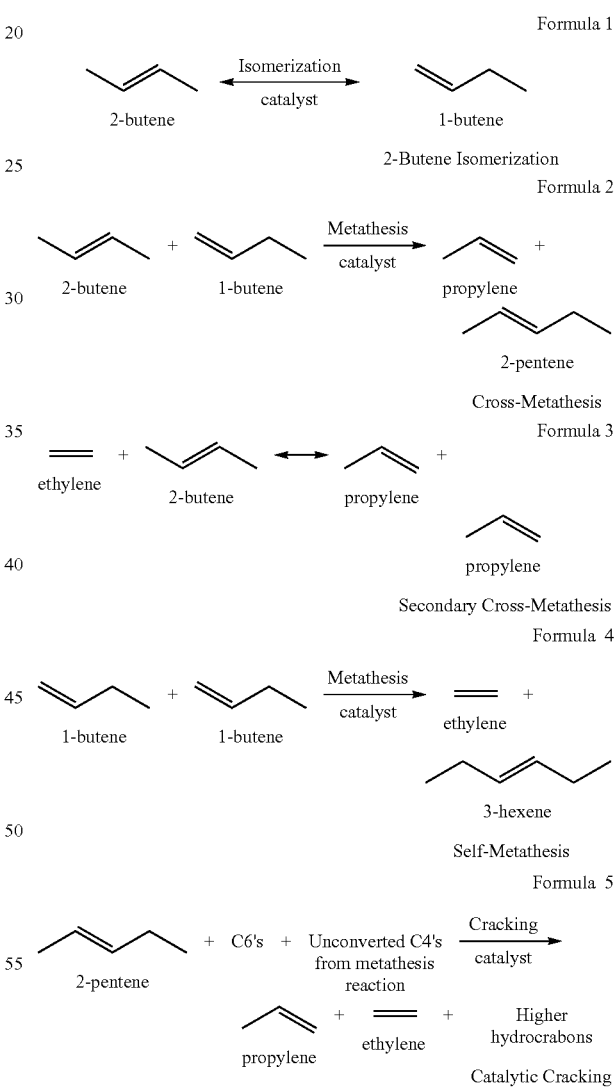

Referring to Formulas 1-5, the "isomerization," "metathesis," and "catalytic cracking" reactions are not limited to these reactants and products; however, Formulas 1-5 provide a basic illustration of the reaction methodology. As shown in Formulas 2-4, metathesis reactions take place between two alkenes. The groups bonded to the carbon atoms of the double bond are exchanged between the molecules to produce two new alkenes with the swapped groups. The specific catalyst that is selected for the olefin metathesis reaction may generally determine whether a cis-isomer or trans-isomer is formed, as the coordination of the olefin molecules with the catalyst play an important role, as do the steric influences of the substituents on the double bond of the newly formed molecule.

In operation, a product stream comprising propylene is produced from a butene containing stream by isomerization, metathesis conversion, and cracking by contacting the butene stream with the multiple-stage catalyst system. The butene stream may comprise 2-butene, and optionally comprises one or more isomers, such as 1-butene, trans-2-butene, and cis-2-butene. The present discussion centers on butene based feed streams; however, it is known that other $C_1$-$C_6$ components may also be present in the feed stream.

In one or more embodiments, the present multiple-stage catalyst system comprises: a silica-alumina catalyst, a mesoporous silica catalyst support impregnated with metal oxide downstream of the silica-alumina catalyst; and a mordenite framework inverted (MFI) structured silica catalyst downstream of the mesoporous silica catalyst. As indicated supra the discussion of a three-stage catalyst system with 3 catalysts is merely for simplicity and a multiple-stage catalyst system with 4 or more catalysts is also envisioned. The silica-alumina catalyst is an isomerization catalyst which facilities isomerization of 2-butene to 1-butene. The mesoporous silica catalyst, which is downstream of the silica-alumina catalyst, is a metathesis catalyst which also facilitates isomerization of 2-butene to 1-butene followed by cross-metathesis of the 2-butene and 1-butene into a metathesis product stream comprising propylene, and other alkenes/alkanes such as pentene. The MFI structured silica catalyst, which is downstream of the metathesis catalyst, is a cracking catalyst which produces propylene from $C_4$ or $C_5$ olefins in the metathesis product stream, and may also yield ethylene.

In one or more embodiments, a first stage comprising the silica-alumina catalyst assists in the isomerization between 2-butene and 1-butene. The second stage comprising the mesoporous silica catalyst contains a metal oxide impregnated on a silica support. The mesoporous silica catalyst performs the butenes to propylene cross-metathesis. The mesoporous silica catalyst may also perform self-metathesis by both isomerizing and metathesizing the butenes. Self-metathesis with the mesoporous silica catalyst is not mandatory for the reaction to proceed as the silica-alumina catalyst already performs the isomerization of the butenes for butene to propylene cross-metathesis by the mesoporous silica catalyst. The third stage comprises the MFI structured catalyst which converts the unreacted $C_4$ hydrocarbons and the produced $C_5$+ hydrocarbons to lighter olefins such as ethylene and propylene. In one or more embodiments, the MFI structured catalyst is a ZSM-5 cracking catalyst.

The ratio of silica to alumina in the silica-alumina catalyst may be varied to provide differing surface area, pore volume, and isomerization performance. In one or more embodiments, the silica-alumina catalyst has a ratio by weight of alumina to silica from about 1:99 to about 20:80. In further embodiments, the silica-alumina catalyst has a ratio by weight of alumina to silica from about 1:99 to about 15:85, or about 2:98 to 10:90, or about 2:98 to 8:12, or about 3:97 to 7:93. It is desirable to minimize the alumina percentage as adding more alumina affects the deactivation and fouling rate of the silica-alumina catalyst. Increased amounts of alumina contribute to deactivation of the silica-alumina catalyst while not significantly enhancing the isomerization activity. As demonstrate by the experimental results in the Examples section of this disclosure, whether you add 5% alumina or 75% alumina to the support of the silica-alumina catalyst, the isomerization activity remains substantially steady.

Maximizing the isomerization of 2-butene to 1-butene by the silica-alumina catalyst improves the overall yield of propylene from the multiple-stage catalyst system. An increased isomerization by the silica-alumina catalyst ensures sufficient availability of both 2-butene and 1-butene for the cross-metathesis reaction by the mesoporous silica catalyst resulting in an ultimate increase in the metathesis product stream for cracking into propylene by the MFI structured silica catalyst. The isomerization of the hydrocarbon feed in the isomerization catalyst zone with the silica-alumina catalyst adjusts the ratio of the various butene isomers (1-butene, 2-cis-butene, trans-2-butene, etc.) to an optimal ratio to perform the subsequent metathesis reactions. The optimal ratio of the various butene isomers directs the reaction toward cross-metathesis instead of undesirable side and skeletal reactions. When the isomerization catalyst zone of the silica-alumina catalyst layer is added, double-bond isomerization reaction occurs, converting the hydrocarbon feed regardless of the initial ratio of 1-butenes and 2-butenes to the optimal ratio. After the isomerization catalyst zone, the metathesis reactions occur in the metathesis catalyst zone. As the feed is already in the right ratio, the metathesis reaction readily occurs in the metathesis catalyst zone of mesoporous silica catalyst. The undesirable skeletal reactions are reduced because there is reduced residual butene left for these undesired reactions to utilize. The cross-metathesis and self-metathesis reactions are faster and more favored than the side reactions. The cross-metathesis is also more favored over the self-metathesis which results in more propylene yield than ethylene yield.

The isomerization may be completed at a broad range of temperatures by the silica-alumina catalyst. The broad temperature range of the silica-alumina catalyst allows the operating temperature of the entire multiple-stage catalyst system to be decreased in comparison to a dual stage catalyst system without the silica-alumina catalyst layer which relies upon self-metathesis by the mesoporous silica catalyst for isomerization of the butenes. Without wishing to be bound by theory, it is believed that the silica-alumina catalyst is capable of performing the isomerization of the butenes at a lesser temperature than the isomerization aspect of self-metathesis by the mesoporous silica catalyst. The lesser reactor operating temperature allowed by the silica-alumina catalyst for isomerization results in an increase in ultimate propylene yield from the multiple-stage catalyst system without creating undesired products, such as isobutene.

Undesirable products may form at higher temperatures as the catalyst in the isomerization zone contains only silica and alumina. Alumina is known to deactivate and crack the feed at higher temperatures, especially when the percent of alumina content is high. When the temperature is increased, the alumina starts to crack the butenes to propylene and ethylene which is undesirable. Also, small amounts of C5s and C6s may be formed in the product. The presence of the undesirable products in the reactor in the metathesis catalyst zone reduces the propylene as well as ethylene rate of formation. Metathesis reactions are controlled by equilibrium, so avoiding propylene, pentene and hexenes in considerable amounts prior to the metathesis catalyst results in preferred propylene formation. Propylene, pentene and hexenes in considerable amounts prior to the metathesis catalyst results in a reaction direction shift from producing primarily propylene to production of butenes from the propylene, pentenes and hexanes present. Furthermore, skeletal isomerization reactions are temperature sensitive where the higher the temperatures, the higher the skeletal activity which results in increased isobutene. When present, isobutene activates side reactions producing undesired products. Besides the undesired products listed previously, running the isomerization catalyst zone at a lower temperature correlates to lesser operating costs due to the reduction in the required heating.

In one or more embodiments, the total pore volume of the silica-alumina catalyst may be from about 0.600 $cm^3/g$ to about 2.5 $cm^3/g$, or about 0.600 $cm^3/g$ to about 1.5 $cm^3/g$, or about 0.600 $cm^3/g$ to about 1.3 $cm^3/g$, or about 0.600 $cm^3/g$ to about 1.1 $cm^3/g$, or about 0.700 $cm^3/g$ to about 1.1 $cm^3/g$, or about 0.800 $cm^3/g$ to about 1.3 $cm^3/g$, or about 0.900 $cm^3/g$ to about 1.2 $cm^3/g$.

Moreover, while broader ranges are contemplated, the silica-alumina catalyst may, in one or more embodiments, include a surface area of about 200 meters$^2$/gram ($m^2/g$) to about 600 $m^2/g$. In further embodiments, the silica-alumina catalyst may have a surface area of from about 225 $m^2/g$ to about 350 $m^2/g$, or about 225 $m^2/g$ to about 325 $m^2/g$, or about 250 $m^2/g$ to about 325 $m^2/g$.

The acidity of the silica-alumina catalyst may be controlled with the amount and selection of alumina precursor in the catalyst precursor solution. Isomerization is affected by the acidity of the silica-alumina catalyst. Acidity is controlled in at least two ways. First, the total number of acidic sites in the silica-alumina catalyst is controlled by the amount of aluminum incorporated into the structure. The more aluminum sites that are present the more Al—OH will be present. Second, the acid strength is also affected by the aluminum sites and how they interact with the silica sites. The source of alumina in the silica-alumina catalyst may have an effect on the formation of various sites. For example: fumed alumina has a large cluster of alumina already formed, therefore the interactions between the alumina and silica are largely predefined and limited to the interface of the two discrete materials. In the case of $Al(NO_3)_3$ the alumina that is created is a single molecule and can potentially interact with silica in all dimensions remaining isolated. Further, in various embodiments, the silica-alumina catalyst may have a total acidity of up to about 0.5 millimole/gram (mmol/g), or about 0.01 mmol/g to about 0.5 mmol/g, or about 0.1 mmol/g to about 0.5 mmol/g, or about 0.3 mmol/g to about 0.5 mmol/g, or about 0.4 mmol/g to about 0.5 mmol/g. It will be appreciated that in further embodiments the silica-alumina catalyst may have a total acidity below 0.01 mmol/g or above 0.5 mmol/g.

Various structures are contemplated for the mesoporous silica catalyst support, for example, a molecular sieve or a zeolite. As used in the application, "mesoporous" means that the silica catalyst support has a narrow pore size distribution. Specifically, the mesoporous silica catalyst support includes a narrow pore size distribution of from about 2.5 nm to about 40 nm and a total pore volume of at least about 0.60 $cm^3/g$. Without being bound by theory, the present pore size distribution and pore volume are sized to achieve better catalytic activity and reduced blocking of pores by metal oxides, whereas smaller pore volume and pore size catalyst systems are susceptible to pore blocking and thereby reduced catalytic activity.

In one or more embodiments, the pore size distribution of the mesoporous silica catalyst support may range from about 2.5 nm to about 40 nm, or about 2.5 nm to about 20 nm, or about 2.5 nm to about 4.5 nm, or about 2.5 nm to about 3.5 nm, or about 8 nm to about 18 nm, or about 12 nm to about 18 nm.

In one or more embodiments, the total pore volume of the mesoporous silica catalyst may be from about 0.600 $cm^3/g$ to about 2.5 $cm^3/g$, or about 0.600 $cm^3/g$ to about 1.5 $cm^3/g$, or about 0.600 $cm^3/g$ to about 1.3 $cm^3/g$, or about 0.600 $cm^3/g$ to about 0.900 $cm^3/g$, or about 0.700 $cm^3/g$ to about 0.900 $cm^3/g$, or about 0.800 $cm^3/g$ to about 1.3 $cm^3/g$.

Moreover, while broader ranges are contemplated, the mesoporous silica catalyst may, in one or more embodiments, include a surface area of about 200 $m^2/g$ to about 600 $m^2/g$. In further embodiments, the mesoporous silica catalyst may have a surface area of from about 225 $m^2/g$ to about 350 $m^2/g$, or about 225 $m^2/g$ to about 325 $m^2/g$, or about 250 $m^2/g$ to about 325 $m^2/g$, or about 250 $m^2/g$ to about 300 $m^2/g$.

Further, the mesoporous silica catalyst may have a total acidity of up to about 0.5 millimole/gram (mmol/g), or about 0.01 mmol/g to about 0.5 mmol/g, or about 0.1 mmol/g to about 0.5 mmol/g, or about 0.3 mmol/g to about 0.5 mmol/g, or about 0.4 mmol/g to about 0.5 mmol/g. Acidity is generally maintained at or less than about 0.5 mmol/g to yield the desired selectivity of propylene and reduced production of undesirable byproducts such as aromatics. Increasing acidity may increase the overall butene conversion; however, this increased conversion may lead to less selectivity and increased production of aromatic byproducts, which can lead to catalyst coking and deactivation.

Furthermore, the mesoporous silica catalyst may have a particle size of from about 20 nm to about 200 nm, or about 50 nm to about 150 nm, or about 75 nm to about 125 nm. In additional embodiments, the mesoporous silica catalyst may have an individual crystal size of about 1 μm to about 200 μm, or about 10 μm to about 150 μm or about 50 μm to about 120 μm.

The catalyst of the cross-metathesis reaction is the impregnated metal oxide of the mesoporous silica catalyst. The metal oxide may comprise one or more oxides of a metal from the Groups 6-10 of the IUPAC Periodic Table. In one or more embodiments, the metal oxide may be an oxide of molybdenum, rhenium, tungsten, or combinations thereof. In a specific embodiment, the metal oxide is tungsten oxide ($WO_3$). It is contemplated that various amounts of metal oxide may be impregnated into the mesoporous silica catalyst support. For example and not by way of limitation, the weight percentage (wt. %) of metal oxide, for example, $WO_3$, in the mesoporous silica catalyst is about 1 to about 30 wt. %, or about 1 to about 25 wt. %, or about 5 to about 20 wt. %, or about 5 to about 15 wt. %, or about 8 to about 12 wt. %. The weight percentage of tungsten in the silica support may be measured by X-ray fluorescence (XRF) or Inductively coupled plasma (ICP).

Additionally, various silica structures are contemplated for the MFI structured silica catalyst. For example, the MFI structured silica catalyst may include MFI structured aluminosilicate zeolite catalysts or MFI structured silica catalysts free of alumina. As used in this disclosure, "free" means less than 0.001% by weight of alumina in the MFI structured silica catalyst. Moreover, it is contemplated that the MFI structured silica catalyst may include other impregnated metal oxides in addition to or as an alternative to alumina. Like the mesoporous silica catalyst, the MFI structured catalysts may have alumina, metal oxides, or both impregnated in the silica support. In addition to or as a substitute for alumina, it is contemplated to include the metal oxides listed prior, specifically, one or more oxides of a metal from Groups 6-10 of the IUPAC Periodic Table, more specifically, metal oxides of molybdenum, rhenium, tungsten, titanium, or combinations thereof.

For the MFI structured aluminosilicate zeolite catalysts, various amounts of alumina are contemplated. In one or more embodiments, the MFI structured aluminosilicate zeolite catalysts may have a molar ratio of silica to alumina of about 5 to about 5000, or about 100 to about 4000, or about 200 to about 3000, or about 1000 to about 2500, or about 1500 to about 2500. Various suitable commercial embodiments of the MFI structured aluminosilicate zeolite catalysts are contemplated, for example, ZSM-5 zeolites such as MFI-280 produced by Zeolyst International or MFI-2000 produced by Saudi Aramco.

Various suitable commercial embodiments are also contemplated for the alumina free MFI structured catalysts. One such example is Silicalite-1 produced by Saudi Aramco.

The MFI structured silica catalyst may include a pore size distribution of from about 1.5 nm to 3 nm, or about 1.5 nm to 2.5 nm. Furthermore, the MFI structured silica catalyst may have a surface area of from about 300 $m^2$/g to about 425 $m^2$/g, or about 340 $m^2$/g to about 410 $m^2$/g. Additionally, the MFI structured silica catalyst may have a total acidity of from about 0.001 mmol/g to about 0.1 mmol/g, or about 0.01 mmol/g to about 0.08 mmol/g. The acidity is maintained equal to or less than about 0.1 mmol/g in order to reduce production of undesirable byproducts such as aromatics. Increasing acidity may increase the amount of cracking; however, this increased cracking may also lead to less selectivity and increased production of aromatic byproducts, which can lead to catalyst coking and deactivation.

In some cases, MFI structured silica catalyst may be modified with an acidity modifier to adjust the level of acidity in the MFI structured silica catalyst. For example, these acidity modifiers may include rare earth modifiers, phosphorus modifiers, potassium modifiers, or combinations thereof. However, as the present embodiments are focused on reducing the acidity to a level at or below 0.1 mmol/g, the present structured silica catalyst may be free of acidity modifier, such as those selected from rare earth modifiers, phosphorus modifiers, potassium modifiers, or combinations thereof. As used in this disclosure, "free of acidity modifiers" means less than less than 0.001% by weight of acidity modifier in the MFI structured silica catalyst.

Further, the MFI structured silica catalyst may have a pore volume of from about 0.1 $cm^3$/g to about 0.3 $cm^3$/g, or about 0.15 $cm^3$/g to about 0.25 $cm^3$/g. Additionally, the MFI structured silica catalyst may have an individual crystal size ranging from about 10 nm to about 40 μm, or from about 15 μm to about 40 μm, or from about 20 μm to about 30 μm. In another embodiment, the MFI structured silica catalyst may have an individual crystal size in a range of from about 1 μm to about 5 μm.

Moreover, various amounts of each catalyst are contemplated for the present multiple-stage catalyst system. For example, it is contemplated that the ratio by volume of the silica-alumina catalyst, the mesoporous silica catalyst, and the MFI structured silica catalyst may range from about 5:1:1 to about 1:5:1 to about 1:1:5, or about 2:1:1 to about 1:2:1 to about 1:1:2, or about 1:1:1.

It is contemplated that the isomerization, the metathesis catalyst, and the cracking catalyst are disposed in one reactor or multiple reactors. For example, it may be desirable to use separate reactors for one or more of the silica-alumina catalyst, the mesoporous silica catalyst, or the MFI structured silica catalyst when they operate at different environmental conditions, including temperature and pressure.

Regardless of whether one or multiple reactors contain the multiple catalysts, the multiple-stage catalyst system will have an isomerization catalyst zone or section, a metathesis catalyst zone or section downstream of the isomerization zone or section, and a cracking catalyst zone or section downstream of the metathesis zone or section. For example, the silica-alumina catalyst may be located in the top part of the reactor, the mesoporous silica metathesis catalyst may be located in the middle part of the reactor, and the MFI structured silica cracking catalyst may be disposed in the bottom part of the reactor, assuming the reactant stream enters the top portion of the reactor. For example, each catalyst may be positioned as discrete catalyst beds. Moreover, it is contemplated that the multiple catalysts of the multiple-stage catalyst system may be in contact with one or more of the other catalysts or separated. However, if the multiple catalysts are in contact, it is desirable that the isomerization catalyst is still disposed upstream of the metathesis catalyst and that the metathesis catalyst is still disposed upstream of the cracking catalyst. The catalysts can be used in the same reactor or with different reactors arranged in series. Alternatively, it is contemplated that the isomerization catalyst (silica-alumina catalyst) is disposed in a first reactor, the metathesis catalyst (mesoporous silica catalyst) is disposed in a separate second reactor downstream of the first reactor, and the cracking catalyst (MFI structured silica catalyst) is disposed in a separate third reactor downstream of the second reactor. Additionally, it is contemplated that the isomerization catalyst (silica-alumina catalyst) is disposed in a first reactor, the cracking catalyst (MFI structured silica catalyst) is disposed in a separate second reactor downstream of the first reactor, and the metathesis catalyst (mesoporous silica catalyst) is disposed in the first reactor downstream of the isomerization catalyst or the second reactor upstream of the cracking catalyst. In specific embodiments, there is a direct conduit between the first reactor and second reactor and the second and third reactor, so that the cracking catalyst can directly crack the product of the butene cross-metathesis reaction.

Various methods of making the catalysts used in the multiple-stage catalyst system are contemplated. Specifically, the processes of wet impregnation and hydrothermal synthesis may be utilized; however, other catalyst synthesis techniques are also contemplated.

Various operating conditions are contemplated for the contacting of the butene stream with the multiple-stage catalyst system. For example, the butene stream may contact the multiple-stage catalyst system at a space hour velocity of about 10 to about 10,000 $h^{-1}$, or about 300 to about 1200 $h^{-1}$. Moreover, the butene stream may contact the catalyst system at a temperature of from about 200 to about 600° C., or about 300 to about 600° C. Furthermore, the butene stream may contact the catalyst system at a pressure from about 1 to about 30 bars, or about 1 to about 10 bars.

Optionally, each of the catalysts in the multiple-stage catalyst system may be pretreated prior to the isomerization, metathesis, and cracking. For example, the multiple-stage catalyst system may be pretreated with $N_2$ for about 1 hour to about 5 hours before isomerization, metathesis, and cracking at a temperature of at least about 400° C., or at least about 500° C.

The product stream yielded by the multiple-stage catalyst system may have at least an 80 mol. % conversion of butene and a propylene yield in mol. % of at least 30%. In a further embodiment, the product stream may have at least an 85 mol. % conversion of butene and a propylene yield in mol. % of the at least 40%. Moreover, the product stream may have at least a 10 mol. % yield of ethylene, or at least a 15 mol. % yield of ethylene, or at least a 20 mol. % yield of ethylene. In yet another embodiment, the product stream may have at least 45 mol. % yield of propylene, or at least about a 50 mol. % yield of propylene.

Moreover, the product stream may comprise less than 1 about wt % aromatics, or less than about 5 wt % of alkanes and aromatics. Without being bound by theory, in some embodiments it may be desirable that the aromatics and alkanes yield be low as it indicates coke formation, which may result in catalyst deactivation.

EXAMPLES

The following examples show the preparation of various catalysts which are used in a combination as in the present multiple catalysts.

Example 1

Preparation of $SiO_2$—$Al_2O_3$ Isomerization Catalyst

To form the $SiO_2$—$Al_2O_3$ catalyst, a total of 20 grams of Q-10 (silica) from Silysia and gamma phase aluminum oxide catalyst support (alumina) from Alfa Aesar were added to a beaker containing 50 milliliters (ml) of deionized (DI) water. The relative amounts of silica and alumina added to the DI water were varied depending on the $SiO_2$—$Al_2O_3$ ratio desired. For example, in the case of 10% $Al_2O_3$ and 90% $SiO_2$, 2 grams of alumina and 18 grams (g) of silica were added to the 50 ml of DI water. The alumina-silica mixture was then mixed used a magnetic stirrer for 2 hours (h) at 580 rotations per minute (rpm). After 2 h, the solution was placed in a rotary evaporator, commonly known as a rotavap. The rotavap was rotated at 171 rpm, and operated under 292 millibar (mbar) vacuum and 80° C. Cold water at 6° C. was pumped into the rotavap housing to enhance condensation. The synthesized material was then placed in a drying oven overnight at 80° C. and calcined at 200° C. for 3 h and then at 575° C. for 5 h. The ramping rate from 200° C. to 575° C. was 3° C. per minute (min).

The XRD patterns of the $SiO_2$—$Al_2O_3$ catalyst with varying ratios of alumina and silica are shown in FIG. 1. The XRD indicates a broad peak centered around 2θ=22.5° indicating the presence of silica in the material. Further, the XRD indicates peaks at approximately 2θ=37°, 38°, 46.3°, and 67° attributable to alumina. The relative strengths of the alumina peaks and the silica peaks for a particular sample is in alignment with the relative ratio of alumina and silica in the $SiO_2$—$Al_2O_3$ catalyst.

Example 2

Preparation of Mesoporous Cross-Metathesis Catalyst ($SiO_2$ Impregnated with a Tungsten Precursor)

In a typical synthesis, $SiO_2$ supports were prepared according to Example 1 with 0% $Al_2O_3$ and 100% $SiO_2$. To synthesize the $SiO_2$ supports with impregnated tungsten precursor, 2 g of the $SiO_2$ support from Example 1 were placed in an 80 ml beaker. 0.235 g of ammonium metatungstate hydrate [$(NH_4)6H_2W_{12}O_{40}.xH_2O$] 99.99% trace metals basis was mixed with 2 ml of DI water. The ammonium metatungstate hydrate was then added drop-wise to the 2 g of $SiO_2$ support. Typically, 5 drops were placed on the $SiO_2$ support. A glass rod was used to thoroughly mix the support. Subsequently, the $SiO_2$ support mixed with the ammonium metatungstate hydrate was placed in a drying oven overnight at 80° C. The dried $SiO_2$ support mixed with the ammonium metatungate hydrate was calcined at 250° C. for 2 h followed by calcining at 550° C. for 8 h with a ramping rate of 1° C. per min until 250° C. was reached and 3° C. per min until 550° C. was reached. This forms mesoporous silica catalyst.

Figure 2:
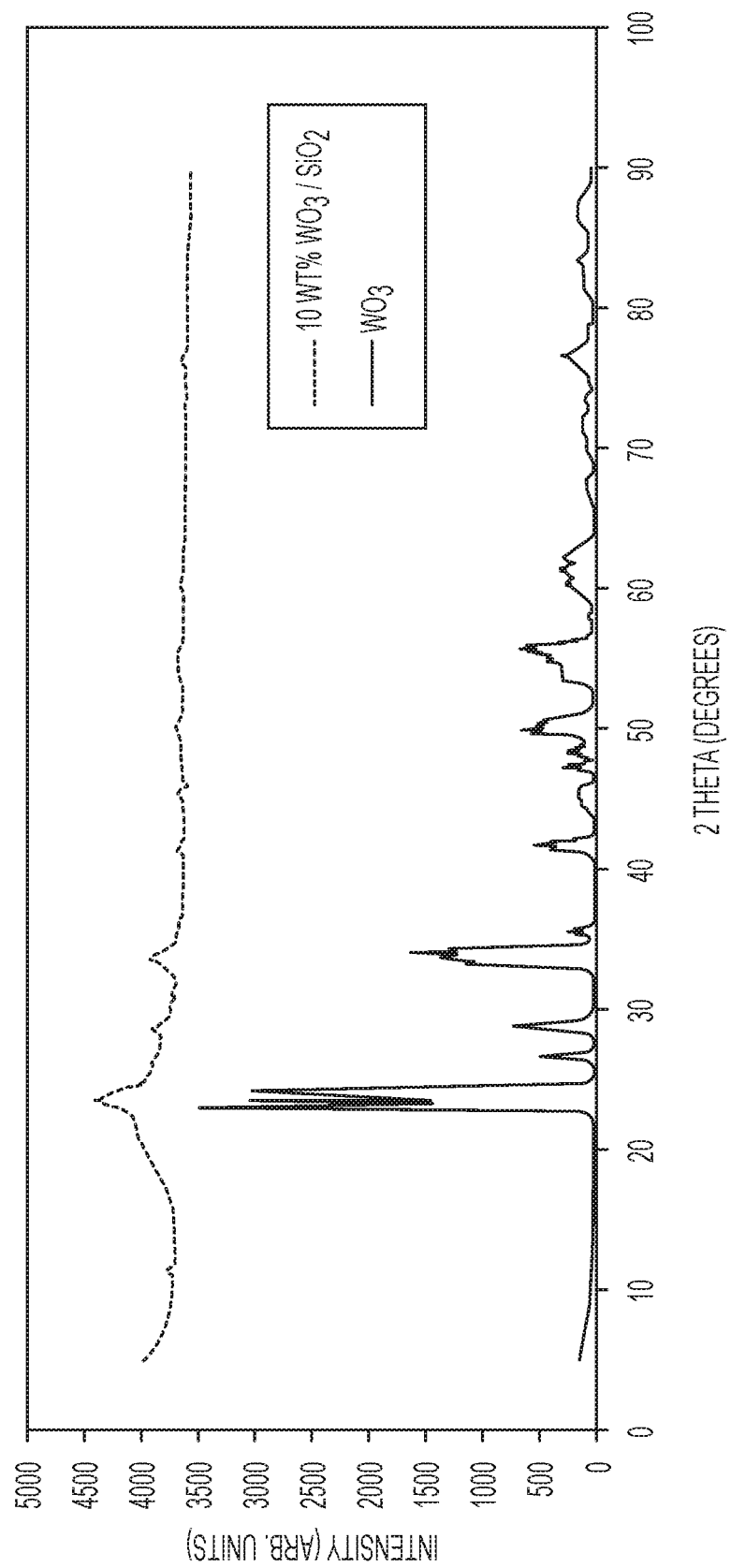
FIG. 2 is an XRD graph of tungsten and a mesoporous silica catalyst comprising a silica support impregnated with tungsten, in accordance with one or more embodiments of the present disclosure.

The XRD patterns of tungsten oxide and a mesoporous silica catalyst ($SiO_2$ support with impregnated tungsten oxide) are shown in FIG. 2. The peaks of the XRD patterns are aligned for the tungsten oxide and the mesoporous silica catalyst indicating the presence of the tungsten oxide in the mesoprous silica catalyst.

Example 3

Preparation of Silicalite-1 Cracking Catalyst

In a typical synthesis, 4.26 g tetrapropylammonium bromide (TPA) and 0.7407 g ammonium fluoride was dissolved in 72 ml of water and stirred well for 15 mins. Then, 12 g fumed silica was added and stirred well until homogenized. The obtained gel was autoclaved and kept at 200° C. for 2 days. The molar composition of gel was 1 $SiO_2$: 0.08 (TPA)Br: 0.10 $NH_4F$: 20 $H_2O$. The solid products obtained were washed with water and dried at 80° C. overnight. The template was removed by calcination in air at 750° C. for 5 hours at a ramping rate of 3° C. per min.

Example 4

Preparation of MFI-2000 Cracking Catalyst

In a typical synthesis, 8.52 g TPA and 1.48 g ammonium fluoride was dissolved in 72 ml of water and stirred well for 20 mins. 24 g fumed silica and 0.15 g of aluminum nitrate were gradually added simultaneously to the TPABr solution while stirring vigorously. Once the solution gelled, the gel was mixed vigorously for about 10 minutes until homogenized. The obtained gel was autoclaved and kept at 200° C. for 2 days. After two days the autoclave was quenched in cold water for 30 minutes. The molar composition of gel was 1 $SiO_2$: 0.0005 $Al_2O_3$: 0.08 (TPA)Br: 0.10 $NH_4F$: 20 $H_2O$. The solid products obtained were washed with water and dried at 80° C. overnight. The template was removed by calcination in air at 750° C. for 6 h with a ramp up of 4° C. per min.

Catalyst Properties

Table 1 includes mechanical properties of the catalysts prepared in Examples 1 and 2.

TABLE 1

| Catalysts/Supports | BET Surface Area (m²/g) | Pore Volume (cm³/g) |
|---|---|---|
| Silica-Alumina Catalyst | | |
| 100% $SiO_2$ - 0% $Al_2O_3$ | 304.41 | 1.13 |
| 95% $SiO_2$ - 5% $Al_2O_3$ | 303.72 | 1.09 |
| 90% $SiO_2$ - 10% $Al_2O_3$ | 305.45 | 0.94 |
| 75% $SiO_2$ - 25% $Al_2O_3$ | 282.37 | 1.00 |
| 50% $SiO_2$ - 50% $Al_2O_3$ | 253.46 | 0.95 |
| 25% $SiO_2$ - 75% $Al_2O_3$ | 231.98 | 0.79 |
| 0% $SiO_2$ - 100% $Al_2O_3$ | 204.82 | 0.70 |
| Mesoporous Silica Catalyst | | |
| $WO_3$/100% $SiO_2$ - 0% $Al_2O_3$ | 374.35 | 0.81 |

Catalyst Evaluation

The prepared catalysts from Examples 1-4 were tested for their activity and selectivity to butene in a fixed bed continuous flow reactor (ID 0.25 in, Autoclave Engineers Ltd.) at atmospheric pressure. A fixed amount of catalyst samples, 1 ml of each catalyst type (with a total of 3 ml) was packed in the reactor tube with silicon carbide at the bottom of the reactor. The silicon carbide is inert and makes no contribution to the reaction chemistry. Each catalyst type and the silicon carbide were separated by quartz wool with an additional layer of quartz wool at the top and bottom of the reactor. The catalysts were pretreated and activated under $N_2$ at 550° C. and a flow of 25 standard cubic centimeters per minute (sccm) for 1 hour. All reactions were carried out at three temperature of 450° C., 500° C., and 550° C., a GHSV (gas hourly space velocity) of 900 $h^{-1}$, and atmospheric pressure using 2-butene (5 milliliters/minutes (ml/min)) as feed with nitrogen as diluent (25 ml/min). The temperature was maintained for 3.5 hours. The quantitative analysis of the reaction products were carried out on-line using an Agilent gas chromatograph with flame ionization detector (FID) (Agilent GC-7890B), equipped with an HP-Al/KCL (50 m×0.53 mm×15 microns) column.

Tables 2-4 indicate the catalytic performance of the silica-alumina catalyst individually. The silica-alumina catalysts were prepared according to Example 1. The silica-alumina catalyst was screened for isomerization activity as well as any propylene production contribution. Each of the silica-alumina catalysts with varying silica to alumina ratios were tested at three temperatures of 500° C., 525° C., and 550° C. represented by Tables 2, 3, and 4 respectively. Values of the yields and conversions of the 2-butene feed were calculated based on an average of values obtained from 5 injections into the gas chromatograph at each temperature.

TABLE 2

| Silica-Alumina Ratio | Ethylene (mol %) | Propylene (mol %) | Trans-Butene (mol %) | 1-Butene (mol %) | Iso-Butene (mol %) | Cis-Butene (mol %) | C5 (mol %) | C6+ (mol %) | Conversion (%) |
|---|---|---|---|---|---|---|---|---|---|
| Temperature = 500° C. | | | | | | | | | |
| 100% $SiO_2$-0% $Al_2O_3$ | 0.00 | 0.00 | 48.55 | 9.07 | 0.25 | 42.16 | 0.00 | 0.00 | 9.29 |
| 95% $SiO_2$-5% $Al_2O_3$ | 0.12 | 0.74 | 37.60 | 27.20 | 6.89 | 27.88 | 0.25 | 0.00 | 34.52 |
| 90% $SiO_2$-10% $Al_2O_3$ | 0.00 | 0.00 | 35.61 | 25.53 | 12.51 | 26.35 | 0.00 | 0.00 | 38.04 |
| 75% $SiO_2$-25% $Al_2O_3$ | 0.00 | 0.88 | 35.21 | 24.81 | 13.66 | 26.07 | 0.14 | 0.00 | 38.73 |
| 50% $SiO_2$-50% $Al_2O_3$ | 0.23 | 1.31 | 32.18 | 24.31 | 15.61 | 24.27 | 1.68 | 0.00 | 43.56 |
| 25% $SiO_2$-75% $Al_2O_3$ | 0.35 | 1.52 | 32.07 | 23.23 | 17.22 | 23.65 | 1.68 | 0.00 | 44.29 |
| 0% $SiO_2$-100% $Al_2O_3$ | 0.08 | 0.50 | 37.24 | 26.65 | 7.40 | 27.59 | 0.60 | 0.00 | 35.17 |

TABLE 3

| Silica-Alumina Ratio | Ethylene (mol %) | Propylene (mol %) | Trans-Butene (mol %) | 1-Butene (mol %) | Iso-Butene (mol %) | Cis-Butene (mol %) | C5 (mol %) | C6+ (mol %) | Conversion (%) |
|---|---|---|---|---|---|---|---|---|---|
| Temperature = 525° C. | | | | | | | | | |
| 100% $SiO_2$-0% $Al_2O_3$ | 0.00 | 0.00 | 48.42 | 9.60 | 0.28 | 41.70 | 0.00 | 0.00 | 9.88 |
| 95% $SiO_2$-5% $Al_2O_3$ | 0.00 | 0.23 | 37.20 | 28.69 | 5.59 | 27.97 | 0.49 | 0.00 | 34.83 |
| 90% $SiO_2$-10% $Al_2O_3$ | 0.00 | 0.00 | 34.27 | 26.06 | 13.43 | 25.56 | 0.69 | 0.00 | 40.18 |
| 75% $SiO_2$-25% $Al_2O_3$ | 0.00 | 0.00 | 34.27 | 25.72 | 13.24 | 25.57 | 1.19 | 0.00 | 40.15 |
| 50% $SiO_2$-50% $Al_2O_3$ | 0.21 | 0.95 | 33.18 | 26.52 | 11.58 | 25.11 | 1.83 | 0.00 | 41.71 |
| 25% $SiO_2$-75% $Al_2O_3$ | 0.00 | 1.07 | 34.27 | 26.14 | 10.72 | 25.71 | 2.86 | 0.00 | 40.03 |
| 0% $SiO_2$-100% $Al_2O_3$ | 0.13 | 0.48 | 37.10 | 28.07 | 4.40 | 27.72 | 1.68 | 0.00 | 35.18 |

TABLE 4

| Silica-Alumina Ratio | Ethylene (mol %) | Propylene (mol %) | Trans-Butene (mol %) | 1-Butene (mol %) | Iso-Butene (mol %) | Cis-Butene (mol %) | C5 (mol %) | C6+ (mol %) | Conversion (%) |
|---|---|---|---|---|---|---|---|---|---|
| Temperature = 550° C. | | | | | | | | | |
| 100% SiO$_2$-0% Al$_2$O$_3$ | 0.00 | 0.00 | 48.18 | 10.43 | 0.32 | 41.07 | 0.00 | 0.00 | 10.75 |
| 95% SiO$_2$-5% Al$_2$O$_3$ | 0.00 | 0.41 | 35.68 | 29.15 | 6.49 | 27.04 | 0.95 | 0.00 | 37.28 |
| 90% SiO$_2$-10% Al$_2$O$_3$ | 0.00 | 0.00 | 32.68 | 26.35 | 14.85 | 24.61 | 1.51 | 0.00 | 42.70 |
| 75% SiO$_2$-25% Al$_2$O$_3$ | 0.00 | 0.77 | 32.60 | 25.90 | 13.66 | 24.57 | 2.51 | 0.00 | 42.84 |
| 50% SiO$_2$-50% Al$_2$O$_3$ | 0.31 | 1.22 | 32.06 | 27.09 | 9.80 | 24.43 | 3.86 | 0.00 | 43.52 |
| 25% SiO$_2$-75% Al$_2$O$_3$ | 0.40 | 1.03 | 31.95 | 25.87 | 9.39 | 24.17 | 6.78 | 0.00 | 43.88 |
| 0% SiO$_2$-100% Al$_2$O$_3$ | 0.14 | 0.70 | 35.01 | 28.38 | 3.35 | 26.66 | 4.60 | 0.00 | 38.33 |

Tables 2-4 demonstrate that increasing the Al$_2$O$_3$ to SiO$_2$ ratio over 10% Al$_2$O$_3$ does not correlate to greater isomerization activity. Specifically, despite increasing the Al$_2$O$_3$ content to 25%, 50%, and 75%, the 1-butene yield remains steady at around 26. Further, the amount of 1-butene formed at each of the three tested temperatures is not substantially different for all seven samples with the exception of the 100% SiO$_2$ catalyst which exhibits a lesser isomerization activity. As the Al$_2$O$_3$ ratio increases, in general the amount of undesired isobutene also increases. Overall, it may be determined from Tables 2-4 that a desirable ratio of Al$_2$O$_3$ to SiO$_2$ is 95% SiO$_2$ and 5% Al$_2$O$_3$ as maximum 1-butene and minimal isobutene is achieved. As a general rule, the higher the alumina content of the catalyst, the quicker the deactivation of the catalyst. While it is noted that the 100% Al$_2$O$_3$ isomerizes a more than the catalysts that contain both silica and alumina, the 100% Al$_2$O$_3$ catalyst is the quickest to deactivate, the tradeoff is not justifiable. Furthermore, the high alumina content catalyst results in cracking and metathesis at higher temperatures, which is undesirable in the isomerization catalyst zone.

Table 5 indicates the catalytic performance of the mesoporous silica catalyst of Example 2. The mesoporous silica catalyst was screened for metathesis activity as well as any propylene production contribution. The mesoporous silica catalyst was tested at three temperatures of 500° C., 525° C., and 550° C. Values of the yields and conversions of the 2-butene feed were calculated based on an average of values obtained from 5 injections into the gas chromatograph at each temperature.

TABLE 5

| Temperature | Ethylene (mol %) | Propylene (mol %) | Trans-Butene (mol %) | 1-Butene (mol %) | Iso-Butene (mol %) | Cis-Butene (mol %) | C5 (mol %) | C6+ (mol %) | Conversion (%) |
|---|---|---|---|---|---|---|---|---|---|
| Sample = 10% WO$_3$/100% SiO$_2$-0% Al$_2$O$_3$ | | | | | | | | | |
| 500° C. | 1.60 | 18.81 | 22.73 | 13.90 | 0.42 | 16.77 | 20.21 | 5.56 | 60.50 |
| 525° C. | 2.58 | 23.53 | 17.88 | 10.48 | 0.29 | 13.25 | 22.28 | 9.70 | 68.86 |
| 550° C. | 3.41 | 25.48 | 16.02 | 10.71 | 0.38 | 12.01 | 21.59 | 10.12 | 71.97 |

Table 5 demonstrates the increasing trend in the yield of desirable propylene formation with temperature increases. Conversely, an increasing trend in the yield of less desirable C$_6$+ hydrocarbons is also observed with temperature increases. As such, running the reactor at 550° C. provides the desirable benefit of an increased propylene production with an acceptable C6+ production given the increased propylene output. Running the reactor at 500° C. is believed to potentially provide the benefit of an increased lifetime of the catalyst bed associated with a lesser operating temperature. The lesser operating temperature in the range of 500° C. still achieves acceptable isomerization activity from the silica-alumina catalyst in conjunction with the acceptable metathesis activity from the mesoporous silica catalyst. In total, operating temperatures of 500° C., 525° C., and 550° C. each exhibit desirable propylene production and demonstrate the wide range of reactor temperatures in which the multiple-stage catalyst system may operate Table 6 indicates the catalytic performance of the MFI structured silica catalyst of Example 4. The tested MFI structured silica catalyst was ZSM-5 with Si/Al=2000 (MFI-2000). The mesoporous silica catalyst was screened for cracking activity as well as any propylene production contribution. The mesoporous silica catalyst was tested at two temperatures of 500° C. and 550° C. Values of the yields and conversions of the 2-butene feed were calculated based on an average of values obtained from 5 injections into the gas chromatograph at each temperature.

TABLE 6

| Temperature | Ethylene (mol %) | Propylene (mol %) | Trans-Butene (mol %) | 1-Butene (mol %) | Iso-Butene (mol %) | Cis-Butene (mol %) | C5 (mol %) | C6+ (mol %) | Conversion (%) |
|---|---|---|---|---|---|---|---|---|---|
| Sample = ZSM-5 | | | | | | | | | |
| 500° C. | 14.343 | 37.773 | 5.865 | 3.925 | 9.867 | 4.284 | 6.946 | 7.401 | 89.852 |
| 550° C. | 17.534 | 41.771 | 5.563 | 4.135 | 8.945 | 4.137 | 4.023 | 6.746 | 90.300 |

Table 6 demonstrates the increasing trend in the yield of desirable propylene formation with temperature increases. Similarly, a decreasing trend in the yield of less desirable C6+ hydrocarbons is also observed with temperature increases. As such, running the reactor at 550° C. provides the desirable benefit of an increased propylene production.

Tables 2-6 provide each of the isomerization, metathesis, and cracking catalysts of Examples 1, 2, and 4 respectively tested separately as single catalyst systems. Specifically, the isomerization, metathesis, and cracking catalysts were individually test without being combined with one or more of the other catalyst type. This provided the effect of the isomerization, metathesis, and cracking catalysts individually to the combined multiple-stage catalyst system with all three of the isomerization, metathesis, and cracking catalysts.

As illustrated in Table 7, a comparative dual catalyst system configurations was also tested. The optimal dual catalyst configuration was a catalyst system consisting of the metathesis catalyst (mesoporous silica catalyst) on the top and the cracking catalyst (MFI structured silica catalyst) in the bottom of the reactor. This configuration represents the multiple-stage catalyst system in the absence of the isomerization catalyst (silica-alumina catalyst). Specifically, the comparative dual catalyst system comprised a mesoporous silica catalyst of 10% $WO_3$/100% $SiO_2$–0% $Al_2O_3$ (Example 2) and a MFI structured silica catalyst of ZSM-5 with a Si/Al ratio equal to 2000 (MFI-2000) (Example 4). This optimized comparative dual catalyst system was subsequently compared to a triple bed catalyst system in accordance with the present disclosure. The triple bed catalyst system was a silica-alumina catalyst of 5% $Al_2O_3$+95% $SiO_2$ (Example 1), a mesoporous silica catalyst of 10% $WO_3$/100% $SiO_2$–0% $Al_2O_3$ (Example 2), and a MFI structured silica catalyst of ZSM-5 with a Si/Al ratio equal to 2000 (MFI-2000) (Example 4).

TABLE 7

| | Triple Catalyst | | | Comparative Dual Catalyst | | | % Change | Yield Difference |
|---|---|---|---|---|---|---|---|---|
| | Temperature ° C. | | | | | | | Triple vs. Double |
| | 450 | 500 | 550 | 450 | 500 | 550 | | |
| | Yield (mol. %) | | | | | | | |
| Methane | 0.000 | 0.114 | 0.300 | 0.000 | 0.101 | 0.238 | | 0.06 |
| Ethane | 0.083 | 0.128 | 0.187 | 0.074 | 0.102 | 0.151 | | 0.04 |
| Ethylene | 8.243 | 11.931 | 16.072 | 7.107 | 10.391 | 14.489 | 11% | 1.58 |
| Propane | 3.365 | 2.436 | 1.727 | 2.801 | 2.232 | 1.727 | | 0.00 |
| Propylene | 33.408 | 39.558 | 44.425 | 33.409 | 38.897 | 43.360 | 2.5% | 1.07 |
| Iso-Butane | 4.532 | 2.101 | 0.889 | 4.101 | 2.324 | 1.131 | | −0.24 |
| N-Butane | 2.629 | 1.521 | 0.880 | 2.430 | 1.710 | 1.039 | | −0.16 |
| Trans-Butene | 6.972 | 6.632 | 6.149 | 7.670 | 2.340 | 7.073 | | −0.92 |
| 1-Butene | 4.414 | 4.763 | 4.957 | 4.117 | 4.402 | 4.579 | | 0.38 |
| Iso-Butene | 12.646 | 11.382 | 10.135 | 13.220 | 12.013 | 10.960 | −8% | −0.82 |
| Cis-Butene | 5.040 | 4.887 | 4.620 | 5.371 | 5.250 | 5.119 | | −0.50 |
| $C_5$ | 10.320 | 7.393 | 4.165 | 13.100 | 10.132 | 6.718 | | −2.55 |
| $C_{6+}$ | 8.366 | 7.153 | 5.493 | 6.537 | 5.126 | 3.418 | | 2.08 |
| Total Olefins ($C_3=$ & $C_2=$) | 41.651 | 51.489 | 60.493 | 40.516 | 49.288 | 57.849 | 5% | 2.65 |
| | Conversion (mol. %) | | | | | | | |
| Conversion | 87.987 | 88.481 | 89.231 | 86.959 | 87.410 | 87.808 | | 1.42 |
| Conversion-$C_4$ | 70.927 | 72.335 | 74.139 | 69.522 | 70.994 | 72.270 | | 1.87 |
| | Selectivity | | | | | | | |
| Propylene Selectivity | 37.986 | 44.709 | 49.787 | 38.420 | 44.301 | 49.379 | 1% | 0.41 |
| Ethylene Selectivity | 9.365 | 13.484 | 18.012 | 8.172 | 11.888 | 16.499 | 9.2% | 1.51 |
| Isobutene Selectivity | 14.373 | 12.864 | 11.358 | 15.203 | 13.744 | 12.481 | −9% | −1.12 |

Table 7 demonstrates the superior performance of the triple bed catalyst system in accordance with the present disclosure over a comparative dual catalyst system. The triple bed catalyst system comprised the dual catalyst system (Examples 2 and 4) with the added isomerization catalyst zone of a silica-alumina catalyst of 5% $Al_2O_3$+95% $SiO_2$ (Example 1). Compared to the dual catalyst system, introduction of the isomerization layer in the triple catalyst system on top of the metathesis and cracking catalyst layers resulted in both the desirable ethylene and propylene yields increasing and the undesirable isobutene yield decreasing.

Figure 3:
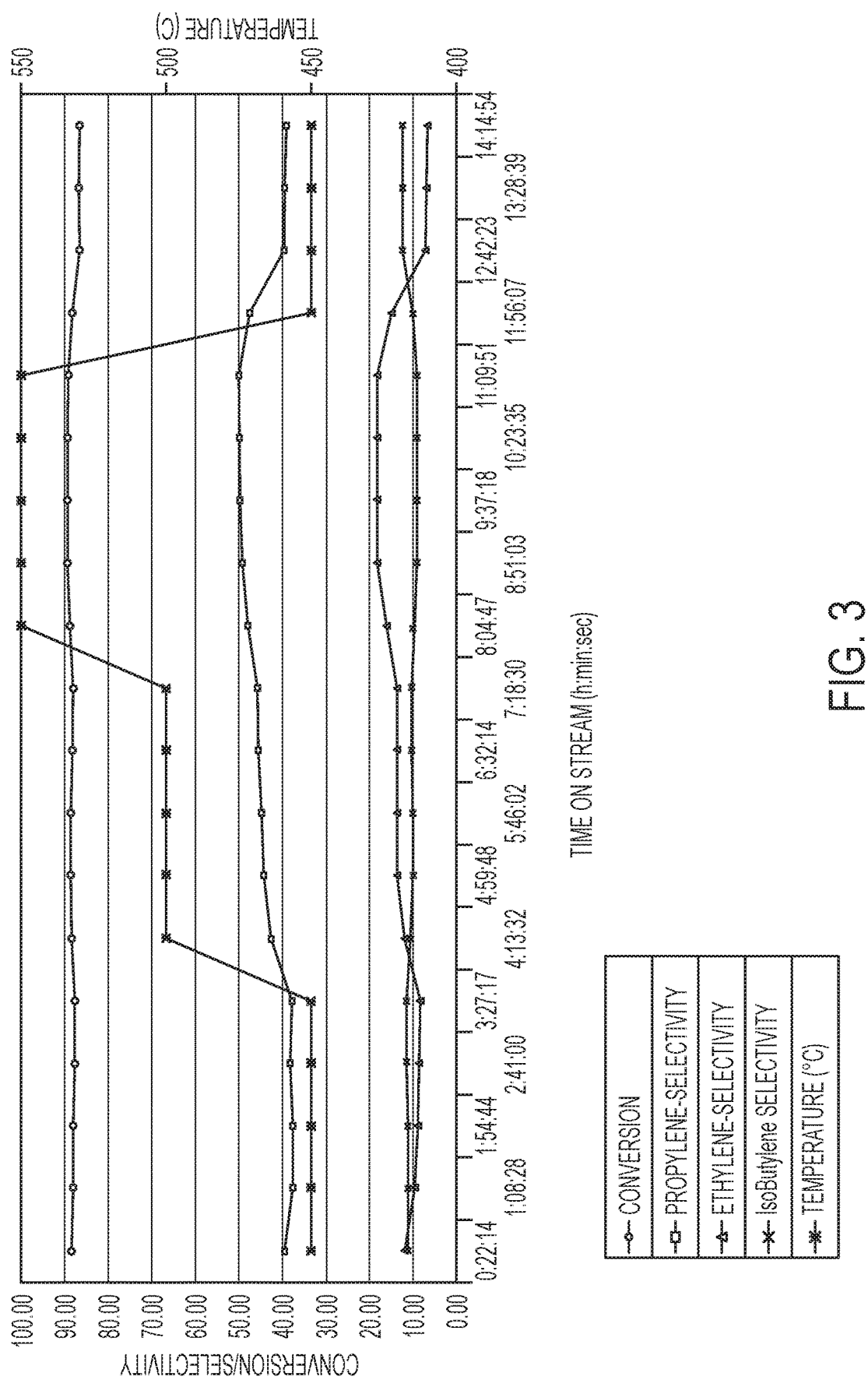
FIG. 3 is a graph illustrating the performance of a multiple-stage catalyst system over time and reaction temperature changes, in accordance with one of more embodiments of the present disclosure.

With reference to FIG. 3, the multiple-stage catalyst system demonstrates a stable conversion and selectivity at various temperatures over a period of time. A triple catalyst system in accordance with the present disclosure (a silica-alumina catalyst of 5% $Al_2O_3$+95% $SiO_2$ (Example 1), a mesoporous silica catalyst of 10% $WO_3$/100% $SiO_2$–0% $Al_2O_3$ (Example 2), and a MFI structured silica catalyst of ZSM-5 with a Si/Al ratio equal to 2000 (MFI-2000) (Example 4)) was utilized for the reaction of 2-butene to propylene at reaction temperatures of 450, 500 and 550° C. at atmospheric pressure with a GHSV of 900 $h^{-1}$. The data of FIG. 3 is also presented as Table 8.

TABLE 8

| | Temperature = 450° C. | | | | |
|---|---|---|---|---|---|
| | Time on Stream | | | | |
| | 0:22:14 | 1:08:28 | 1:54:44 | 2:41:00 | 3:27:17 |
| Conversion | 88.39 | 88.10 | 88.05 | 87.70 | 87.71 |
| Propylene Selectivity | 39.35 | 37.36 | 37.37 | 38.17 | 37.59 |
| Ethylene Selectivity | 11.73 | 9.63 | 8.73 | 8.54 | 8.19 |
| IsoButene Selectivity | 10.95 | 11.01 | 11.01 | 11.33 | 11.33 |

TABLE 8-continued

| | Temperature = 500° C. | | | | |
|---|---|---|---|---|---|
| | Time on Stream | | | | |
| | 4:13:32 | 4:59:48 | 5:46:02 | 6:32:14 | 7:18:30 |
| Conversion | 88.37 | 88.63 | 88.61 | 88.2 | 88.11 |
| Propylene Selectivity | 42.47 | 44.09 | 44.61 | 45.43 | 45.64 |
| Ethylene Selectivity | 11.84 | 13.47 | 13.49 | 13.48 | 13.34 |
| IsoButene Selectivity | 10.39 | 9.97 | 9.95 | 10.30 | 10.39 |

| | Temperature = 550° C. | | | | |
|---|---|---|---|---|---|
| | Time on Stream | | | | |
| | 8:04:47 | 8:51:03 | 9:37:18 | 10:23:35 | 11:09:51 |
| Conversion | 88.78 | 89.37 | 89.33 | 89.26 | 89.20 |
| Propylene Selectivity | 47.98 | 49.15 | 49.66 | 49.73 | 49.84 |
| Ethylene Selectivity | 16.03 | 18.13 | 18.18 | 18.09 | 17.93 |

TABLE 8-continued

| IsoButene Selectivity | 9.59 | 8.98 | 8.97 | 9.02 | 9.07 |

Temperature = 450° C. (Return)

Time on Stream

| | 11:56:07 | 12:42:23 | 13:28:39 | 14:14:54 |
|---|---|---|---|---|
| Conversion | 88.28 | 86.50 | 86.54 | 86.43 |
| Propylene Selectivity | 47.45 | 39.69 | 39.44 | 39.15 |
| Ethylene Selectivity | 14.86 | 7.15 | 6.81 | 6.61 |
| IsoButene Selectivity | 10.10 | 12.21 | 12.24 | 12.35 |

Table 9 indicates the catalytic performance of a triple bed catalyst system in accordance with this disclosure. Specifically, a silica-alumina catalyst of 5% $Al_2O_3$+95% $SiO_2$ (Example 1), a mesoporous silica catalyst of 10% $WO_3$/100% $SiO_2$–0% $Al_2O_3$ (Example 2), and a MFI structured silica catalyst of ZSM-5 with a Si/Al ratio equal to 2000 (MFI-2000) (Example 4) were utilized in combination. The effect of varying the amount of the isomerization catalyst (Example 1) was determined. The triple catalyst system was run with 1 ml of each catalyst in the triple catalyst system and was also run with 2 ml of the silica-alumina catalyst and 1 ml of each of the MFI structured silica catalyst and mesoporous silica catalyst. The comparative test determined that the overall catalyst performance remains substantially unchanged when the isomerization catalyst is increased by a factor of 2. The slight decrease in propylene yield is attributed to the resulting change in the hourly space velocity from the increased isomerization catalyst.

Calculation Methodologies

Determination of "% Change" was calculated according to formula 1.

$$\frac{\text{yield@550 C for triple bed} - \text{yield@550 C for dual bed}}{\text{yield@550 C for dual bed}} \times 100 \qquad (1)$$

Determination of "Conversion" was calculated according to formula 2, where $n_i$ is the number of moles of component "i" entering or leaving the reactor.

$$\text{Conversion} = \frac{n_{i,in} - n_{i,out}}{n_{i,in}} \times 100 \qquad (2)$$

Similarly, determination of "Conversion-C4" was calculated according to formula 3.

Conversion-C4=100−(CisButene Yield+TransButene Yield+IsoButene Yield+1-Butene Yield)  (3)

Determination of "Selectivity" was calculated according to formula 4.

$$\text{Selectivity} = \frac{\text{Yield of Product}}{\text{Conversion}} \times 100 \qquad (4)$$

The surface area of the samples was measured by nitrogen adsorption at 77 K using AUTOSORB-1 (Quanta Chrome). Before adsorption measurements, samples (ca. 0.1 g) were heated at 220° C. for 2 hours under nitrogen flow. The nitrogen adsorption isotherms of catalysts were measured at liquid nitrogen temperature (77 K). The surface areas was

TABLE 9

| | 1 ml Silica-Alumina Catalyst + 1 ml Mesoporous Silica Catalyst + 1 ml MFI Structured Catalyst | | | 2 ml Silica-Alumina Catalyst + 1 ml Mesoporous Silica Catalyst + 1 ml MFI Structured Catalyst | | |
|---|---|---|---|---|---|---|
| | Temperature ° C. | | | | | |
| | 450 | 500 | 550 | 450 | 500 | 550 |
| | Yield (mol. %) | | | | | |
| Methane | 0.000 | 0.114 | 0.300 | 0.000 | 0.114 | 0.294 |
| Ethane | 0.083 | 0.128 | 0.187 | 0.083 | 0.127 | 0.188 |
| Ethylene | 8.243 | 11.931 | 16.072 | 8.233 | 11.731 | 15.991 |
| Propane | 3.365 | 2.436 | 1.727 | 3.373 | 2.393 | 1.828 |
| Propylene | 33.408 | 39.558 | 44.425 | 32.853 | 39.270 | 43.810 |
| Iso-Butane | 4.531 | 2.201 | 0.889 | 4.547 | 2.118 | 1.022 |
| N-Butane | 2.629 | 1.521 | 0.880 | 2.582 | 1.551 | 0.997 |
| Trans-Butene | 6.972 | 6.632 | 6.149 | 7.109 | 6.792 | 6.297 |
| 1-Butene | 4.414 | 4.763 | 4.957 | 4.180 | 4.565 | 4.775 |
| Iso-Butene | 12.646 | 11.382 | 10.135 | 12.695 | 11.457 | 10.204 |
| Cis-Butene | 5.040 | 4.887 | 4.620 | 5.080 | 4.941 | 4.683 |
| $C_5$ | 10.320 | 7.393 | 4.165 | 10.702 | 7.659 | 4.405 |
| $C_6$+ | 8.366 | 7.153 | 5.493 | 8.580 | 7.283 | 5.507 |
| Total Olefins ($C_3$= & $C_2$=) | 41.651 | 51.489 | 60.498 | 41.087 | 51.001 | 59.801 |
| | Conversion (mol. %) | | | | | |
| Conversion | 87.987 | 88.481 | 89.231 | 87.812 | 88.267 | 89.020 | calculated by the Brunauer Emmett-Teller (BET) method. The total pore volume was estimated from the amount of $N_2$ adsorbed at P/P0=0.99. Barret E P, Joyner L J, Halenda P H, J. Am. Chem. Soc. 73 (1951) 373-380.

In a first aspect, the disclosure provides a process for production of propylene comprising introducing a hydrocarbon stream comprising 2-butene to an isomerization catalyst zone to isomerize the 2-butene to 1-butene, where the isomerization catalyst zone comprises a silica-alumina catalyst with a ratio by weight of alumina to silica from 1:99 to 20:80; passing the 2-butene and 1-butene to a metathesis catalyst zone to cross-metathesize the 2-butene and 1-butene into a metathesis product stream comprising propylene and $C_4$-$C_6$ olefins, where the metathesis catalyst comprises a mesoporous silica catalyst support impregnated with metal oxide; and cracking the metathesis product stream in a catalyst cracking zone to produce propylene, where the catalyst cracking zone comprises a mordenite framework inverted (MFI) structured silica catalyst.

In a second aspect, the disclosure provides a process of the first aspect, in which the silica-alumina catalyst includes a surface area of 200 $m^2$/g to 600 $m^2$/g.

In a third aspect, the disclosure provides a process of either the first or second aspects, in which the silica-alumina catalyst includes a surface area of 250 $m^2$/g to 325 $m^2$/g.

In a fourth aspect, the disclosure provides a process of any one of the first through third aspects, in which the silica-alumina catalyst has a pore volume of at least 0.60 $cm^3$/g.

In a fifth aspect, the disclosure provides a process of any one of the first through fourth aspects, in which the silica-alumina catalyst has a pore volume of 0.90 $cm^3$/g to 1.2 $cm^3$/g.

In a sixth aspect, the disclosure provides a process of any one of the first through fifth aspects, in which the silica-alumina catalyst comprises an alumina to silica weight ratio between 1:99 and 10:90.

In a seventh aspect, the disclosure provides a process of any one of the first through sixth aspects, in which the silica-alumina catalyst comprises an alumina to silica weight ratio between 3:97 and 7:93.

In an eighth aspect, the disclosure provides a process of any one of the first through seventh aspects, in which the metal oxide of the mesoporous silica catalyst comprises one or more oxides of molybdenum, rhenium, tungsten, or combinations thereof.

In a ninth aspect, the disclosure provides a process of any one of the first through eighth aspects, in which the metal oxide of the mesoporous silica catalyst is tungsten oxide ($WO_3$).

In a tenth aspect, the disclosure provides a process of any one of the first through ninth aspects, in which the mesoporous silica catalyst comprises 1 to 30 weight percent tungsten oxide.

In an eleventh aspect, the disclosure provides a process of any one of the first through tenth aspects, in which the mesoporous silica catalyst comprises 8 to 12 weight percent tungsten oxide.

In a twelfth aspect, the disclosure provides a process of any one of the first through eleventh aspects, in which the mesoporous silica catalyst includes a surface area of 200 $m^2$/g to 600 $m^2$/g.

In a thirteenth aspect, the disclosure provides a process of any one of the first through twelfth aspects, in which the mesoporous silica has a pore volume of at least 0.60 $cm^3$/g.

In a fourteenth aspect, the disclosure provides a process of any one of the first through thirteenth aspects, in which the MFI structured silica catalyst includes a total acidity of 0.001 mmol/g to 0.1 mmol/g.

In a fifteenth aspect, the disclosure provides a process of any one of the first through fourteenth aspects, in which the MFI structured silica catalyst comprises alumina.

In a sixteenth aspect, the disclosure provides a process of any one of the first through fourteenth aspects, in which the MFI structured silica catalyst is alumina free.

In a seventeenth aspect, the disclosure provides a process of any one of the first through fifteenth aspects, in which the MFI structured silica catalyst comprises ZSM-5.

In an eighteenth aspect, the disclosure provides a process of any one of the first through seventeenth aspects, in which the hydrocarbon feed is a Raffinate 2 stream from a fluid catalytic cracker or an ethylene cracker.

In a nineteenth aspect, the disclosure provides a process of any one of the first through seventeenth aspects, in which the hydrocarbon feed is a Raffinate 2 stream which consists of 45 to 55 wt % 1-butene, 20 to 30 wt % 2-butene, 10 to 20 wt % n-butane, 5 to 15 wt % iso-butane, and 0 to 5 wt % other components.

In a twentieth aspect, the disclosure provides a process of any one of the first through seventeenth aspects, in which the hydrocarbon feed is a Raffinate 2 stream which consists of 10 to 20 wt % 1-butene, 20 to 30 wt % 2-butene, 8 to 18 wt % n-butane, 37 to 47 wt % iso-butane, and 0 to 8 wt % other components.

In an twenty-first aspect, the disclosure provides a multiple-stage catalyst system for producing propylene from a hydrocarbon stream, the multiple-stage catalyst system comprising an isomerization catalyst zone, a metathesis catalyst zone downstream of the isomerization zone, and a cracking catalyst zone downstream of the metathesis catalyst zone; where the isomerization catalyst zone comprises a silica-alumina catalyst with a ratio by weight of alumina to silica from 1:99 to 20:80, where the silica-alumina catalyst zone isomerizes the 2-butene to 1-butene; the metathesis catalyst zone comprises a mesoporous silica catalyst support impregnated with metal oxide to form a mesoporous silica catalyst, where the mesoporous silica catalyst zone cross-metathesizes the 2-butene and 1-butene into a metathesis product stream comprising propylene and $C_4$-$C_6$ olefins; and the cracking catalyst zone comprises a mordenite framework inverted (MFI) structured silica catalyst, where the cracking catalyst zone cracks the metathesis product stream to produce propylene.

In a twenty-second aspect, the disclosure provides a multiple-stage catalyst system of the twenty-first aspect, in which the isomerization catalyst zone, the metathesis catalyst zone, and the cracking catalyst zone are disposed in one reactor.

In a twenty-third aspect, the disclosure provides a multiple-stage catalyst system of the twenty-first aspect, in which the isomerization catalyst zone is disposed on a first reactor, the metathesis catalyst zone is disposed in a second reactor downstream of the first reactor, and the cracking catalyst zone is disposed in a third reactor downstream of the second reactor.

In a twenty-fourth aspect, the disclosure provides a multiple-stage catalyst system of the twenty-first aspect, in which the isomerization catalyst zone is disposed on a first reactor, the cracking catalyst zone is disposed in a second reactor downstream of the first reactor, and the metathesis catalyst zone is disposed in the first reactor downstream of the isomerization catalyst zone or in the second reactor upstream of the cracking catalyst zone.

In a twenty-fifth aspect, the disclosure provides a multiple-stage catalyst system of any one of the twenty-first through twenty-fourth aspects, in which the silica-alumina catalyst includes a surface area of 200 m²/g to 600 m²/g.

In a twenty-sixth aspect, the disclosure provides a multiple-stage catalyst system of any one of the twenty-first through twenty-fifth aspects, in which the silica-alumina catalyst includes a surface area of 250 m²/g to 325 m²/g.

In a twenty-seventh aspect, the disclosure provides a multiple-stage catalyst system of any one of the twenty-first through twenty-fifth aspects, in which the silica-alumina catalyst has a pore volume of at least 0.60 cm²/g.

In a twenty-eighth aspect, the disclosure provides a multiple-stage catalyst system of any one of the twenty-first through twenty-sixth aspects, in which the silica-alumina catalyst has a pore volume of 0.90 cm³/g to 1.2 cm³/g.

In a twenty-ninth aspect, the disclosure provides a multiple-stage catalyst system of any one of the twenty-first through twenty-eighth aspects, in which the silica-alumina catalyst comprises an alumina to silica weight ratio between 1:99 and 10:90.

In a thirtieth aspect, the disclosure provides a multiple-stage catalyst system of any one of the twenty-first through twenty-ninth aspects, in which the silica-alumina catalyst comprises an alumina to silica weight ratio between 3:97 and 7:93.

In a thirty-first aspect, the disclosure provides a multiple-stage catalyst system of any one of the twenty-first through thirtieth aspects, in which where the metal oxide of the mesoporous silica catalyst comprises one or more oxides of molybdenum, rhenium, tungsten, or combinations thereof.

In a thirty-second aspect, the disclosure provides a multiple-stage catalyst system of any one of the twenty-first through thirty-first aspects, in which the metal oxide of the mesoporous silica catalyst is tungsten oxide ($WO_3$).

In a thirty-third aspect, the disclosure provides a multiple-stage catalyst system of any one of the twenty-first through thirty-second, in which the mesoporous silica catalyst comprises 8 to 12 weight percent tungsten oxide.

In a thirty-fourth aspect, the disclosure provides a multiple-stage catalyst system of any one of the twenty-first through thirty-third aspects, in which the mesoporous silica catalyst includes a surface area of 200 m²/g to 600 m²/g.

In a thirty-fifth aspect, the disclosure provides a multiple-stage catalyst system of any one of the twenty-first through thirty-fourth aspects, in which the mesoporous silica catalyst includes a surface area of 250 m²/g to 300 m²/g.

In a thirty-sixth aspect, the disclosure provides a multiple-stage catalyst system of any one of the twenty-first through thirty-fifth aspects, in which the mesoporous silica catalyst has a pore volume of at least 0.60 cm³/g.

In a thirty-seventh aspect, the disclosure provides a multiple-stage catalyst system of any one of the twenty-first through thirty-sixth aspects, in which the mesoporous silica catalyst has a pore volume of 0.80 cm³/g to 1.3 cm³/g.

In a thirty-eighth aspect, the disclosure provides a multiple-stage catalyst system of any one of the twenty-first through thirty-seventh aspects, in which the MFI structured silica catalyst includes a total acidity of 0.001 mmol/g to 0.1 mmol/g.

In a thirty-ninth aspect, the disclosure provides a multiple-stage catalyst system of any one of the twenty-first through thirty-eighth aspects, in which the MFI structured silica catalyst comprises alumina.

In a fortieth aspect, the disclosure provides a multiple-stage catalyst system of any one of the twenty-first through thirty-ninth aspects, in which the MFI structured silica catalyst is alumina free.

In a forty-first aspect, the disclosure provides a multiple-stage catalyst system of any one of the twenty-first through thirty-ninth aspects, in which the MFI structured silica catalyst comprises ZSM-5.

Throughout this disclosure ranges are provided for various parameters and characteristics of the catalysts and multiple-stage catalyst system. It will be appreciated that when one or more explicit ranges are provided the individual values and the ranges formed therebetween are also intended to be provided as providing an explicit listing of all possible combinations is prohibitive. For example, a provided range of 1-10 also includes the individual values, such as 1, 2, 3, 4.2, and 6.8, as well as all the ranges which may be formed within the provided bounds, such as 1-8, 2-4, 6-9, and 1.3-5.6.

It should now be understood that various aspects of the systems and methods of making propylene with the multiple catalysts are described and such aspects may be utilized in conjunction with various other aspects. It should also be understood to those skilled in the art that various modifications and variations can be made to the described embodiments without departing from the spirit and scope of the claimed subject matter. Thus, it is intended that the specification cover the modifications and variations of the various described embodiments provided such modification and variations come within the scope of the appended claims and their equivalents.

What is claimed is:

1. A multiple-stage catalyst system for producing propylene from a hydrocarbon stream comprising 2-butene, the multiple-stage catalyst system comprising an isomerization catalyst zone, a metathesis catalyst zone downstream of the isomerization zone, and a cracking catalyst zone downstream of the metathesis catalyst zone where:
   the isomerization catalyst zone comprises a silica-alumina catalyst with a ratio by weight of alumina to silica from 1:99 to 20:80, where the silica-alumina catalyst zone isomerizes the 2-butene to 1-butene;
   the metathesis catalyst zone comprises a mesoporous silica catalyst support impregnated with metal oxide to form a mesoporous silica catalyst, where the mesoporous silica catalyst zone cross-metathesizes the 2-butene and 1-butene into a metathesis product stream comprising propylene and $C_4$-$C_6$ olefins;
   the cracking catalyst zone comprises a mordenite framework inverted (MFI) structured silica catalyst, where the cracking catalyst zone cracks the metathesis product stream to produce propylene; and
   the MFI structured catalyst is directly downstream of the mesoporous silica catalyst such that the metathesis product stream is passed directly from the mesoporous silica catalyst to the MFI structured silica catalyst.

2. The multiple-stage catalyst system of claim 1 where the isomerization catalyst zone, the metathesis catalyst zone, and the cracking catalyst zone are disposed in one reactor.

3. The multiple-stage catalyst system of claim 1 where the isomerization catalyst zone is disposed in a first reactor, the metathesis catalyst zone is disposed in a second reactor downstream of the first reactor, the cracking catalyst zone is disposed in a third reactor downstream of the second reactor, and a direct conduit extends between the second reactor and the third reactor.

4. The multiple-stage catalyst system of claim 1 where the isomerization catalyst zone is disposed in a first reactor, the cracking catalyst zone is disposed in a second reactor downstream of the first reactor, and the metathesis catalyst zone is disposed in the first reactor downstream of the isomerization catalyst zone with a direct conduit extending between the first reactor and the second reactor or in the second reactor directly upstream of the cracking catalyst zone.

5. The multiple-stage catalyst system of claim 1 where the silica-alumina catalyst includes a surface area of 200 m$^2$/g to 600 m$^2$/g.

6. The multiple-stage catalyst system of claim 1 where the silica-alumina catalyst has a pore volume of at least 0.60 cm$^2$/g.

7. The multiple-stage catalyst system of claim 1 where the silica-alumina catalyst comprises an alumina to silica weight ratio between 1:99 and 10:90.

8. The multiple-stage catalyst system of claim 1 where the metal oxide of the mesoporous silica catalyst comprises one or more oxides of molybdenum, rhenium, tungsten, or combinations thereof.

9. The multiple-stage catalyst system of claim 1 where the metal oxide of the mesoporous silica catalyst is tungsten oxide (WO$_3$).

10. The multiple-stage catalyst system of claim 1 where the mesoporous silica catalyst has a pore volume of at least 0.60 cm$^3$/g.

11. The multiple-stage catalyst system of claim 1 where the MFI structured silica catalyst includes a total acidity of 0.001 mmol/g to 0.3 mmol/g.

* * * * *

UNITED STATES PATENT AND TRADEMARK OFFICE
CERTIFICATE OF CORRECTION

PATENT NO. : 10,550,048 B2
APPLICATION NO. : 15/873421
DATED : February 4, 2020
INVENTOR(S) : Faisal H. Alshafei et al.

Page 1 of 1

It is certified that error appears in the above-identified patent and that said Letters Patent is hereby corrected as shown below:

On the Title Page

Item (72), Inventor "Munir D. Khokhar", country of residence, delete "(DE)" and insert --(SA)--, therefor.

Signed and Sealed this
Twenty-sixth Day of May, 2020

Andrei Iancu
*Director of the United States Patent and Trademark Office*